(12) United States Patent
Kakkis

(10) Patent No.: US 9,089,566 B2
(45) Date of Patent: *Jul. 28, 2015

(54) DELIVERY OF THERAPEUTIC COMPOUNDS TO THE BRAIN AND OTHER TISSUES

(75) Inventor: Emil D. Kakkis, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/399,787

(22) Filed: Feb. 17, 2012

(65) Prior Publication Data

US 2012/0148558 A1    Jun. 14, 2012

Related U.S. Application Data

(63) Continuation of application No. 11/630,446, filed as application No. PCT/US2004/028135 on Aug. 30, 2004, which is a continuation of application No. 10/651,493, filed on Aug. 29, 2003, now Pat. No. 7,442,372.

(51) Int. Cl.
*A61K 38/47* (2006.01)

(52) U.S. Cl.
CPC ...................................... *A61K 38/47* (2013.01)

(58) Field of Classification Search
None
See application file for complete search history.

(56) References Cited

U.S. PATENT DOCUMENTS

| | | | |
|---|---|---|---|
| 4,801,575 A * | 1/1989 | Pardridge | 514/1.2 |
| 5,716,614 A | 2/1998 | Katz et al. | |
| 5,929,304 A | 7/1999 | Radin et al. | |
| 5,981,194 A | 11/1999 | Jefferies et al. | |
| 6,002,067 A | 12/1999 | Clarke et al. | |
| 6,149,909 A | 11/2000 | Scott et al. | |
| 6,217,552 B1 | 4/2001 | Barbut et al. | |
| 6,238,662 B1 | 5/2001 | Scott et al. | |
| 6,426,208 B1 | 7/2002 | Kakkis et al. | |
| 6,455,494 B1 | 9/2002 | Jefferies et al. | |
| 6,458,574 B1 | 10/2002 | Selden et al. | |
| 6,524,835 B1 | 2/2003 | Scott et al. | |
| 6,534,300 B1 | 3/2003 | Canfield | |
| 6,537,785 B1 | 3/2003 | Canfield | |
| 6,569,661 B1 | 5/2003 | Qin et al. | |
| 6,582,692 B1 | 6/2003 | Podsakoff et al. | |
| 6,585,971 B1 | 7/2003 | Kakkis | |
| 6,972,124 B2 | 12/2005 | Qin et al. | |
| 7,396,811 B2 * | 7/2008 | LeBowitz et al. | 514/1.2 |
| 7,442,372 B2 | 10/2008 | Kakkis | |
| 7,485,314 B2 | 2/2009 | Kakkis et al. | |
| 7,883,707 B2 | 2/2011 | Kakkis et al. | |
| 2002/0028195 A1 | 3/2002 | Coffey et al. | |
| 2002/0095135 A1 | 7/2002 | Meeker et al. | |
| 2003/0072761 A1 | 4/2003 | LeBowitz | |
| 2003/0077806 A1 | 4/2003 | Selden et al. | |
| 2004/0009906 A1 | 1/2004 | Kakkis et al. | |
| 2005/0042227 A1 | 2/2005 | Zankel et al. | |
| 2005/0142141 A1 | 6/2005 | Pardridge | |

FOREIGN PATENT DOCUMENTS

| | | |
|---|---|---|
| WO | WO-01/36603 A2 | 5/2001 |
| WO | WO-0185200 A2 | 11/2001 |
| WO | WO-02/05841 A1 | 1/2002 |
| WO | WO-03/086452 A2 | 10/2003 |
| WO | WO-03/090695 A2 | 11/2003 |
| WO | WO-2004/091475 A2 | 10/2004 |
| WO | WO-2005/002515 A2 | 1/2005 |

OTHER PUBLICATIONS

Yu et al. Short-Term Enzyme Replacement in the Murine Model of Sanfilippo Syndrome Type B. Mol Genet Metab. Dec. 2000;71(4):573-80.*
Intrathecal (Wikipedia entry, retrieved Jan. 28, 2014 from http://en.wikipedia.org/wiki/Intrathecal).*
Ammaya, Subcutaneous reservoir and pump for sterile access to ventricular cerebrospinal fluid. Lancet, 2(7315):983-4 (1963).
Barranger et al., Gene transfer approaches to the lysosomal storage disorders. *Neurochem. Res.*, 24(4):601-15 (1999).
Bembi et al., Cerebrospinal fluid infusion of alglucerase in the treatment of acute neuronopathic Gaucher's Disease, Abstract #14, Eur Soc for Ped Res attachment. *Pediatric Res.*, 38:A425 (1995).
Bickel et al., Delivery of peptides and proteins through the blood-brain barrier. *Adv. Drug Deliv. Rev.*, 46(1-3):247-79 (2001).
Bobo et al., Convection-enhanced delivery of macromolecules in the brain. *Proc. Natl. Acad. Sci. U.S.A.*, 91(6):2076-80 (1994).
Bowes et al., Continuous intrathecal fluid infusions elevate nerve growth factor levels and prevent functional deficits after spinal cord ischemia. *Brain Res.*, 883(2):178-83 (2000).
Broadwell et al., Transcytosis of protein through the mammalian cerebral epithelium and endothelium. III. Receptor-mediated transcytosis through the blood-brain barrier of blood-borne transferring and antibody against the receptor. *Exp. Neurol.*, 142(1):47-65 (1996).
Chavany et al., Biology and potential strategies for the treatment of GM2 gangaliosidoses. *Mol. Med. Today*, 4(4):158-65 (1998).
Daly et al., Neonatal gene transfer leads to widespread correction of pathology in a murine model of lysosomal storage disease. *Proc. Natl. Acad. Sci. U.S.A.*, 96(5):2296-300 (1999).

(Continued)

*Primary Examiner* — Gregory S Emch

(74) *Attorney, Agent, or Firm* — Marshall, Gerstein & Borun LLP

(57) ABSTRACT

The present invention relates to the intrathecal (IT) administration of recombinant enzyme to treat lysosomal storage disorders. In an exemplary embodiment, intrathecal administration of human α-L-iduronidase (rhIDU) injections in MPS I affected animals resulted in significant enzyme uptake, significant rh-iduronidase activity in brain and meninges and a decrease of glycosaminoglycan (GAG) storage in cells of MPS I subjects to that of normal subjects. Intrathecal administration proved more effective than intravenous treatment at alleviating MPS I symptoms, indicating it is a useful method of treating lysosomal storage disorders.

12 Claims, 15 Drawing Sheets

(56) References Cited

OTHER PUBLICATIONS

Daly et al., Neonatal intramuscular injection with recombinant adeno-associated virus results in prolonged beta-glucuronidase expression in situ and correction of liver pathology in mucopolysaccharidosis type VII mice. *Hum. Gene Ther.*, 10(1):85-94 (1999).

Daniele et al., Uptake of recombinant iduronate-2-sulfatase into neuronal and glial cells in vitro. *Biochim. Biophys. Acta*, 1588(3):203-9 (2002).

Dehouck et al., A new function for the LDL receptor: transcytosis of LDL across the blood-brain barrier. *J. Cell. Biol.*, 138(4):877-89 (1997).

Dittrich et al., Pharmacokinetics of intrathecally applied BDNF and effects on spinal motoneurons. *Exp. Neurol.*, 141 (2):225-39 (1996).

Eikelboom et al., Homocyst(e)ine and cardiovascular disease: a critical review of the epidemiologic evidence. *Ann. Intern. Med.*, 131 (5):363-75 (1999).

Elliger et al., Elimination of lysosomal storage in brains of MPS VII mice treated by intrathecal administration of an adeno-associated virus vector. *Gene Ther.*, 6(6):1175-8 (1999).

Elliger et al., Enhanced secretion and uptake of beta-glucuronidase improves adeno-associated viral-mediated gene therapy of mucopolysaccharidosis type VII mice. *Mol. Ther.*, 5(5):617-26 (2002).

Farndale et al., A direct spectrophotometric microassay for sulfated glycosaminoglycans in cartilage cultures. *Connect Tissue Res.*, 9(4):247-8 (1982).

Fillebeen et al., Receptor-mediated transcytosis of lactoferrin through the blood-brain barrier. *J. Biol. Chem.*, 274(11):7011-7 (1999).

Fukuta et al., Insulin fragments as a carrier for peptide delivery across the blood-brain barrier. *Pharm. Res.*, 11(12):1681-8 (1994).

Ghodsi, Extensive beta-glucuronidase activity in murine central nervous system after adenovirus-mediated gene transfer to brain. *Hum. Gene Ther.*, 9(16):2331-40 (1998).

Godel et al., Visual functions in Tay Sachs diseased patients following enzyme replacement therapy. *Metab. Ophthalmol.*, 2:27-32 (1978).

Guidotti et al., Adenoviral gene therapy of the Tay-Sachs disease in hexosaminidase A-deficient knock-out mice. *Hum. Mol. Genet.*, 8(5):831-8 (1999).

Hartung et al., Enzymatic correction and cross-correction of mucopolysaccharidosis type I fibroblasts by adeno-associated virus-mediated transduction of the alpha-L-iduronidase gene. *Hum. Gene Ther.*, 10(13):2163-72 (1999).

Jensen et al., Retrovirus-mediated gene transfer of ornithine-delta-aminotransferase into keratinocytes from gyrate atrophy patients. *Hum. Gene Ther.*, 8(17):2125-32 (1997).

Jones et al., Human mucopolysaccharidosis IIID: clinical, biochemical, morphological and immunohistochemical characteristics. *J. Neuropathol. Exp. Neurol.*, 56(10):1158-67 (1997).

Kakkis et al., Enzyme replacement therapy in feline mucopolysaccharidosis I. *Mol. Genet. Metab.*, 72(3):199-208 (2001).

Kakkis et al., Enzyme-replacement therapy in mucopolysaccharidosis I. *N. Engl. J. Med.*, 344(3):182-8 (2001).

Kakkis et al., Intrathecal enzyme replacement therapy reduces lysosomal storage in the brain and meninges of the canine model of MPS I. *Mol. Genet. Metab.*, 83(1-2):163-74 (2004).

Kakkis et al., Long-term and high-dose trials of enzyme replacement therapy in the canine model of mucopolysaccharidosis I. *Biochem. Mol. Med.*, 58(2):156-67 (1996).

Koliatsos et al., Recombinant human nerve growth factor prevents retrograde degeneration of axotomized basal forebrain cholinergic neurons in the rat. *Exp. Neurol.*, 112(2):161-73 (1991).

Kusuhara et al., Efflux transport systems for drugs at the blood-brain barrier and blood-cerebrospinal fluid barrier (Part 1). *Drug Discov. Today*, 6(3):150-6 (2001).

Lazorthes et al., Advances in drug delivery systems and applications in neurosurgery. *Adv. Tech. Stand. Neurosurg.*, 18:143-92 (1991).

Li et al., Molecular basis of iduronate-2-sulphatase gene mutations in patients with mucopolysaccharidosis type II (Hunter syndrome). *J. Med. Genet.*, 36(1):21-7 (1999).

Locorazza et al., Correction of ornithine-delta-aminotransferase deficiency in a Chinese hamster ovary cell line mediated by retrovirus gene transfer. *Gene Ther.*, 2(1):22-8 (1995).

Lutzko et al., Gene therapy for canine alpha-L-iduronidase deficiency: in utero adoptive transfer of genetically corrected hematopoietic progenitors results in engraftment but not amelioration of disease. *Hum. Gene Ther.*, 10(9):1521-32 (1999).

McGill et al., Detection of heterozygotes for recessive alleles. Homocyst(e)inemia: paradigm of pitfalls in phenotypes. *Am. J. Med. Genet.*, 36(1):45-52 (1990).

McIntyre, Laronidase treatment of mucopolysaccharidosis I. *Drugs of the Future*, 28(5):432-4 (2003).

Nguyen et al., Convective distribution of macromolecules in the primate brain demonstrated using computerized tomography and magnetic resonance imaging. *J Neurosurg.*, 98(3):584-90 (2003).

Northover et al., Mucopolysaccharidosis type IVA (Morquio syndrome): a clinical review. *J. Inherit. Metab. Dis.*, 19(3):357-65 (1996).

Ochs et al., A phase I/II trial of recombinant methionyl human brain derived neurotrophic factor administered by intrathecal infusion to patients with amyotrophic lateral sclerosis. *Amyotroph. Lateral Scler. Other Motor Neuron Disord.*, 1(3):201-6 (2000).

Ommaya, Implantable devices for chronic access and drug delivery to the central nervous system. *Cancer Drug Deliv.*, 1(2):169-79 (1984).

Pardridge, Blood-brain barrier biology and methodology. *J. Neurovirol.*, 5(6):556-69 (1999).

Penn et al., The office-based elective surgery center. *Neurosurgery*, 40(1):94-9 (1997).

Pfister et al., Expression of beta-glucuronidase haplotypes in prototype and congenic mouse strains. *Biochem. Genet.*, 20(5-6):519-36 (1982).

Poorthuis et al., Bone marrow transplantation has a significant effect on enzyme levels and storage of glycosaminoglycans in tissues and in isolated hepatocytes of mucopolysaccharidosis type VII mice. *Pediatr. Res.*, 36(2):187-93 (1994).

Rathmann et al., Mucopolysaccharidosis type II (Hunter syndrome): mutation "hot spots" in the iduronate-2-sulfatase gene. *Am. J. Hum. Genet.*, 59(6):1202-9 (1996).

Rivero et al., Retrovirus-mediated gene transfer and expression of human ornithine delta-aminotransferase into embryonic fibroblasts. *Hum. Gene Ther.*, 5(6):701-7 (1994).

Sands et al., Murine mucopolysaccharidosis type VII: long term therapeutic effects of enzyme replacement and enzyme replacement followed by bone marrow transplantation. *J Clin. Invest.*, 99(7):1596-1605 (1997).

Scott et al., Cloning of the sulphamidase gene and identification of mutations in Sanfilippo A syndrome. *Nat. Genet.*, 11(4):465-7 (1995).

Shull et al., Enzyme replacement in a canine model of Hurler syndrome. *Proc. Natl. Acad. Sci. U.S.A.*, 91(26):12937-41 (1994).

Smith et al., Pharmacokinetics and tolerability of ventricularly administered superoxide dismutase in monkeys and preliminary clinical observations in familial ALS. *J. Neurol. Sci.*, 129 Suppl:13-8 (1995).

Stein et al., Systemic and central nervous system correction of lysosomal storage in mucopolysaccharidosis type VII mice. *J. Virol.*, 73(4):3424-9 (1999).

Stroncek et al., Retroviral transduction and expansion of peripheral blood lymphocytes for the treatment of mucopolysaccharidosis type II, Hunter's syndrome. *Transfusion*, 39(4):343-50 (1999).

Takenaka et al., Circulating alpha-galactosidase A derived from transduced bone marrow cells: relevance for corrective gene transfer for Fabry disease. *Hum. Gene Ther.*, 10(12):1931-9 (1999).

Takenaka et al., Enzymatic and functional correction along with long-term enzyme secretion from transduced bone marrow hematopoietic stem/progenitor and stromal cells derived from patients with Fabry disease. *Exp. Hematol.*, 27(7):1149-59 (1999).

(56) References Cited

OTHER PUBLICATIONS

Tsuji et al., Carrier-mediated or specialized transport of drugs across the blood-brain barrier. *Adv. Drug Deliv. Rev.*, 36(2-3):277-90 (1999).
Villani et al., Maroteaux-lamy syndrome: five novel mutations and their structural localization. *Biochim. Biophys. Acta*, 1453(2):185-92 (1999).
Vogler et al., A murine model of mucopolysaccharidosis VII. Gross and microscopic findings in beta-glucuronidase-deficient mice. *Am. J. Pathol.*, 136(1):207-17 (1990).
Von Specht et al., Enzyme replacement in Tay-Sachs disease. *Neurology*, 29(6):848-54 (1979).
Watanabe et al., Mice deficient in cystathionine beta-synthase: animal models for mild and severe homocyst(e)inemia. *Proc. Natl. Acad. Sci. U.S.A.*, 92(5):1585-9 (1995).
Watson et al., Treatment of lysosomal storage disease in MPS VII mice using a recombinant adeno-associated virus. *Gene Ther.*, 5(12):1642-9 (1998).
Yogalingam et al., Evaluation of fibroblast-mediated gene therapy in a feline model of mucopolysaccharidosis type VI. *Biochim. Biophys. Acta*, 1453(2):284-96 (1999).
Ziegler et al., Correction of enzymatic and lysosomal storage defects in Fabry mice by adenovirus-mediated gene transfer. *Hum. Gene Ther.*, 10(10):1667-82 (1999).
Zirzow et al., Delivery, distribution, and neuronal uptake of exogenous mannose-terminal glucocerebrosidase in the intact rat brain. *Neurochem. Res.*, 24(2):301-5 (1999).

International Preliminary Report on Patentability for International Application No. PCT/US04/28135, dated Feb. 28, 2006.
International Search Report for International Application No. PCT/US04/28135, dated Jun. 29, 2005.
Supplemental European Search Report, EP04782579, dated Jun. 19, 2009.
Written Opinion for the International Search Authority for International Application No. PCT/US04/28135, dated Jun. 29, 2005.
Kaemmerer et al., Intrathecal Delivery of Aldurazyme® (Iaronidase) in Normal Canines: A Comparison of Enzyme Elevation in CNS Tissue Resulting from Chronic or Intermittent Bolus Delivery, 2006 Lysosomal Diseases and the Brain Conference, Organized by the Children's Gaucher Research Fund, Speaker Abstract (2006).
Final Office Action, U.S. Appl. No. 12/991,104, notification date Mar. 14, 2013.
Haskell et al., Viral-mediated delivery of the late-infantile neuronal ceroid lipofuscinosis gene, TPP-I to the mouse central nervous system, *Gene Ther.*, 10(1):34-42 (2003).
Lin et al., Production and characterization of recombinant human CLN2 protein for enzyme-replacement therapy in late infantile neuronal ceroid lipofuscinosis, *Biochem. J.*, 357(Pt. 1):49-55 (2001).
Non-final office action, U.S. Appl. No. 11/630,446, dated Jul. 19, 2013.
Non-final office action, U.S. Appl. No. 11/630,446, dated Jan. 27, 2014.
Nonfinal Office Action, U.S. Appl. No. 12/991,104, notification date Oct. 12, 2012.
Sondhi et al., Feasibility of gene therapy for late neuronal ceroid lipofuscinosis, *Arch. Neurol.*, 58:1793-8 (2001).

\* cited by examiner

Mean rhIDU Level in Normal Dogs following different doses IT x4

Iduronidase in the Brain, Spinal Cord and Meninges Following Four Weekly Injections Comparison of Brain GAG Content in IT and IV treated MPS Animals Neuron Disease by EM, With and Without 4 x 1 mg IT doses Meningeal Disease, With and Without 4 x 1mg IT doses

DELIVERY OF THERAPEUTIC COMPOUNDS TO THE BRAIN AND OTHER TISSUES

This application is a continuation of U.S. patent application Ser. No. 11/630,446, filed Aug. 22, 2008, which is a U.S. national phase of Int'l Application No. PCT/US2004/028135, filed Aug. 30, 2004, which claims priority to U.S. patent application Ser. No. 10/651,493, filed Aug. 29, 2003.

FIELD OF THE INVENTION

The present invention relates to the intrathecal (IT) administration of recombinant enzyme to treat lysosomal storage disorders. Further contemplated is the induction of antigen specific tolerance prior to intrathecal administration of replacement enzyme.

BACKGROUND OF THE INVENTION

The brain is shielded against potentially harmful substances by the blood-brain barrier (BBB). The microvascular barrier between blood and brain is made up of a capillary endothelial layer surrounded by a basement membrane and tightly associated accessory cells (pericytes, astrocytes). The brain capillary endothelium is much less permeable to low-molecular weight solutes than other capillary endothelia due to an apical band of tight association between the membranes of adjoining cells, referred to as tight junctions. In addition to diminished passive diffusion, brain capillary endothelia also exhibit less fluid-phase pinocytosis than other endothelial cells. Brain capillaries possess few fenestrae and few endocytic vesicles, compared to the capillaries of other organs (see Pardridge, *J. Neurovirol.* 5: 556-569 (1999)). There is little transit across the BBB of large, hydrophilic molecules aside from some specific proteins such as transferrin, lactoferrin and low-density lipoproteins, which are taken up by receptor-mediated endocytosis (see Pardridge, *J. Neurovirol.* 5: 556-569 (1999)); Tsuji and Tamai, *Adv. Drug Deliv. Rev.* 36: 277-290 (1999); Kusuhara and Sugiyama, *Drug Discov. Today* 6:150-156 (2001); Dehouck, et al. *J. Cell. Biol.* 138: 877-889 (1997); Fillebeen, et al. *J. Biol. Chem.* 274: 7011-7017 (1999)).

The blood-brain barrier (BBB) also impedes access of beneficial active agents (e.g., therapeutic drugs and diagnostic agents) to central nervous system (CNS) tissues, necessitating the use of carriers for their transit. Blood-brain barrier permeability is frequently a rate-limiting factor for the penetration of drugs or peptides into the CNS (see Pardridge, *J. Neurovirol.* 5: 556-569 (1999); Bickel, et al., *Adv. Drug Deliv. Rev.* 46: 247-279 (2001)). For example, management of the neurological manifestations of lysosomal storage diseases (LSDs) is significantly impeded by the inability of therapeutic enzymes to gain access to brain cell lysosomes. LSDs are characterized by the absence or reduced activity of specific enzymes within cellular lysosomes, resulting in the accumulation of undegraded "storage material" within the intracellular lysosome, swelling and malfunction of the lysosomes, and ultimately cellular and tissue damage. Intravenous enzyme replacement therapy (ERT) is beneficial for LSDs (e.g. MPS I, MPS II). However, the BBB blocks the free transfer of many agents from blood to brain, and LSDs that present with significant neurological sequelae (e.g. MPSI, MPS III, MLD, GM1) are not expected to be as responsive to intravenous ERT. For such diseases, a method of delivering the replacement enzyme across the BBB and into the lysosomes of the affected cells would be highly desirable.

There are several ways of circumventing the BBB to enhance brain delivery of an administered active agent include direct intra-cranial injection, transient permeabilization of the BBB, and modification of the active agent to alter tissue distribution. Direct injection of an active agent into brain tissue bypasses the vasculature completely, but suffers primarily from the risk of complications (infection, tissue damage) incurred by intra-cranial injections and poor diffusion of the active agent from the site of administration. Permeabilization of the BBB entails non-specifically compromising the BBB concomitant with injection of intravenous active agent and is accomplished through loosening tight junctions by hyperosmotic shock (e.g. intravenous mannitol). High plasma osmolarity leads to dehydration of the capillary endothelium with partial collapse of tight junctions, little selectivity in the types of blood-borne substances that gain access to the brain under these conditions, and damage over the course of a life-long regimen of treatment.

The distribution of an active agent into the brain may also be increased by transcytosis, the active transport of certain proteins from the luminal space (blood-side) to the abluminal space (brain-side) of the BBB. Transcytosis pathways are distinct from other vesicular traffic within the capillary endothelial cell and transit can occur without alteration of the transported materials. Transcytosis is a cell-type specific process mediated by receptors on the BBB endothelial surface. Attachment of an active agent to a transcytosed protein (vector or carrier) is expected to increase distribution of the active substance to the brain. In transcytosis, the vector is presumed to have a dominant effect on the distribution of the joined pair. Vector proteins include antibodies directed at receptors on the brain capillary endothelium (Pardridge, *J. Neurovirol.* 5: 556-569 (1999)) and ligands to such receptors (Fulcuta, et al., 1994, *Pharm Res.* 1994; 11(12):1681-8; Broadwell, et al., *Exp Neurol.* 1996; 142(1):47-65)). Antibody vectors are transported through the capillary endothelium by a process of adsorptive endocytosis (non-specific, membrane-phase endocytosis) and are far less efficiently transported than actual receptor ligands, which cross the BBB by a saturable, energy-dependent mechanism (Broadwell, et al., *Exp Neurol.* 1996; 142(1):47-65).

Direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., *Proc. Natl. Acad. Sci. U.S.A* 91, 2076-2080 (1994); Nguyen, et al. *J. Neurosurg.* 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has yielded only moderate success in a few examples of delivery via the CSF [Dittrich et al., *Exp. Neurol.* 141:225-239 (1996); Ochs et al., *Amyotroph. Lateral. Scler. Other Motor Neuron Disord.* 1:201-206 (2000); Bowes et al., *Brain Res.* 883:178-183 (2000)]. For nerve growth factor (NGF), the administration of the factor into the ventricle of the brain, did have some beneficial effects on the brain (Koliatsos et al., *Exp. Neurol.* 112, 161-173 (1991), but did not show significant diffusion into the brain substance. A major challenge in this treatment has been the tendency of the factor to bind the ependymal lining of the ventricle very tightly which prevented subsequent diffusion. Currently, there are no approved products for the treatment of brain genetic disease by therapeutic administration directly to the CSF.

The challenges in treating the brain with these and other therapeutics studied in the past have suggested that the barrier to diffusion at the brain's surface, as well as the lack of diffusion and efficacy of brain treatment, were too great an obstacle to achieve adequate therapeutic effect in the brain for any disease. Prior evidence suggests that intraventricular or intrathecal enzyme therapy would not work sufficiently to be effective, and in fact, no human studies of this approach have been published in the recent past and there are no successful examples of treatment via that route. Intrathecal injection confers an advantage over other standard treatment regimens, however, in that the CSF provides superior access to the brain and meninges. The CSF covers the brain and provides large surface area contact with cortical neurons up to 6 mm below the surface, allowing for more efficient penetration of the therapeutic into the brain tissue.

Lysosomal storage disorders affecting the nervous system demonstrate unique challenges in treating these diseases with traditional therapies. There is often a large build-up of glycosaminoglycans (GAGs) in neurons and meninges of affected individuals, leading to either mild or severe forms of the disease. For example, brain disease in severe MPS I patients is characterized by developmental delay, hydrocephalus, severe mental retardation, and eventual decline and death due to disease symptoms. Mild MPS I brain is characterized by perivascular GAG storage, hydrocephalus, learning disabilities and spinal cord compression due to swelling and scarring from storage disease. In MPS I patients in which meningeal storage is affected, the meninges are obstructed, reducing CSF resorption and leading to high pressure hydrocephalus. This aberrant lysosomal storage also leads to thickening and scarring of the meninges from storage disease.

In the lysosomal storage disorder, Gaucher disease, patients with the severe fat of the disease (type 2 and type 3) have brain disease and intravenous enzyme therapy is insufficient to effectively and adequately treat the brain. Intrathecal and intraparenchymal enzyme therapy with glucocerebrosidase, the enzyme deficient in Gaucher disease, has succeeded in getting into the brain but did not successfully treat the brain storage (Zirzow et al., *Neurochem. Res.* 24,: 301-305. 1999). At this time, no brain disease resulting from a lysosomal disorder has successfully been treated by any means available.

Thus, there remains a need in the art to develop methods which effectively treat lysosomal storage disorders through effective administration of enzyme replacement therapy. More particularly, a need exists for more effective methods of administration of compounds and compositions that can more efficiently deliver active agents to the brain and central nervous system for the treatment of lysosomal storage disorders.

SUMMARY OF THE INVENTION

The present invention is directed to methods and compositions for the treatment of central nervous system manifestations of enzyme storage diseases. More particularly, the present invention is based on the discovery that intrathecal delivery of compositions comprising enzymes that are deficient or lacking in lysosomal storage disorders, results in sustained, long-term clinically useful therapeutic intervention of the central nervous system manifestations of such diseases. Thus, the present invention is directed to enzyme replacement therapy for such diseases by intrathecal administration into the cerebrospinal fluid of subjects in need of such therapy.

Accordingly, in one aspect of the present invention, there is provided a method of treating a lysosomal storage disease comprising providing a pharmaceutical composition comprising a protein defective or missing in the lysosomal storage disease; and delivering the pharmaceutical composition into the cerebrospinal fluid the subject, whereby the protein is delivered at a level which provides a therapeutic effect in the mammalian subject. More particularly, the method generally comprises delivery of the protein to the brain tissue of the subject at a level which provides a therapeutic effect in the mammalian subject. More specifically, the delivery to the cerebrospinal fluid is achieved by intrathecal injection.

In particularly preferred embodiments, the methods of the present invention provide for the intrathecal administration of iduronidase to effect a therapeutic intervention of MPS. This treatment has a beneficial effect on the subject, as it reduces or eliminates glycogen storage granules in tissues. Moreover, intrathecal injection of the enzyme into the cerebrospinal fluid of both neonatal and adult subjects, results in therapeutic levels of iduronidase in the brain and the reduction or elimination of glycosaminoglycan storage granules in brain tissue.

While certain embodiments use iduronidase as the enzyme being replaced, it should be understood that the methods of the present invention may be used for the therapeutic intervention of other diseases that require the administration of a different enzyme. For example, the present invention also contemplates intrathecal administration of beta-glucuronidase (MPS VII), iduronate sulfatase S II), alpha-N-acetylglucosaminidase (MPS IIIB), arylsulfatase A (MLD), glucocerebrosidase, β-glucosidase or N-acetylgalactosamine 4-sulfatase.

Further, it is contemplated that the presence on the cell surface of brain cells of a high affinity receptor for the uptake of the enzyme, even at low concentrations of the enzyme will produce a concentration gradient in the CSF that drives the enzyme to traverse the brain's surface across the brain-CSF interface.

In preferred embodiments, the present invention is directed to a method for treating a lysosomal storage disease in a mammal comprising intrathecal administration into the central nervous system of the mammal a pharmaceutical composition comprising an enzyme that is deficient in the lysosomal storage disease in an amount effective to ameliorate the symptoms of the lysosomal storage disease. Those of skill in the art routinely monitor subjects for symptoms of lysosomal storage disease through routine assessment of history, physical examination, echocardiography, electrocardiography, magnetic resonance imaging, polysomnography, skeletal survey, range of motion measurements, corneal photographs, and skin biopsy (see U.S. Pat. No. 6,585,971). Any such methods may be used in conjunction with the treatment methods of the present invention.

Preferably, the enzyme replacement therapy pharmaceutical composition is administered in an amount effective to decrease the amount of storage granules present in the brain tissue of the mammal. More particularly, the therapy results in a reduction of GAG build-up in the neuronal and/or meningeal tissue of the subject. In certain preferred methods of the invention, the therapeutic intervention ameliorates high pressure hydrocephalus associated with lysosomal storage disease.

Preferably, the intrathecal administration of the enzyme therapy of the present invention produces a reduction in meningeal swelling that results from the presence of lysosomal storage granules in the meninges of individuals suffering from lysosomal storage disease.

The methods of the present invention may be used for the treatment of any lysosomal storage disease which manifests an effect in brain or meningeal tissue and requires the medicament to enter the brain or meninges. The methods of the present application, achieve a therapeutic effect by crossing the brain-CSF interface and ameliorating the deleterious effects of the lysosomal storage disease in brain tissue. For example, such a disease may include, but is not limited to aspartylglucosaminuria, cholesterol ester storage disease, Wolman disease, cystinosis, metachromatic leukodystrophy, Danon disease, Fabry disease, Farber lipogranulomatosis, Farber disease, fucosidosis, galactosialidosis types I/II, Gaucher disease types I/II/III, Gaucher disease, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leukodystrophy, mucolipidosis type I, sialidosis types I/II mucolipidosis types II/III I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB Morquio syndrome, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types A/B, Niemann-Pick disease, Niemann-Pick disease type C1, Niemann-Pick disease type C2, pycnodysostosis, Schindler disease types I/II, Schindler disease, and sialic acid storage disease.

In particularly preferred embodiments, the disease is mucopolysaccharidosis, and more preferably, the disease is mucopolysaccharidosis I. In certain embodiments, the subject with the lysosomal storage disease has a diminished normal α-L-iduronidase activity. The activity may be diminished because the enzyme is mutated or absent in the subject. In particular embodiment, the mammal has about 50% or less of a normal α-L-iduronidase activity. In other embodiments, the subject has 75% or less of a normal α-L-iduronidase activity. In order to treat this deficiency, the methods of the present invention may employ a pharmaceutical composition which comprises a dose of at least about 125,000 units or 0.5 mg/kg of the human α-L-iduronidase. Other preferred doses include between about 0.01 mg/15-20 kg body weight of the subject to about 10 mg/15-20 kg body weight of the subject. The dose may be administered in any convenient dose and at any conveniently spaced interval determined by the physician administering the treatment. In certain embodiments, the enzyme replacement therapy is administered weekly to a subject suffering from a deficiency in a lysosomal storage enzyme.

In certain exemplary embodiments, the pharmaceutical composition comprises a dose of at least about dose of between about 0.01 mg/15 cc of CSF to about 5.0 mg/15 cc of CSF in the mammal of the human α-L-iduronidase is administered weekly to a subject suffering from a deficiency thereof. Preferably, the pharmaceutical composition comprises a dose of about 1 mg/15 cc of CSF in the mammal of the human α-L-iduronidase is administered weekly to a subject suffering from a deficiency thereof. An exemplary pharmaceutical composition is formulated in a buffer comprising 0.58 mg/ml iduronidase in a buffer comprising 100 mM sodium phosphate, 150 mM NaCl and 0.001% polysorbate 80.

The pharmaceutical compositions for use in the methods of the present invention also may contain other components, such as for example, human albumin. In particular embodiments, the compositions contain human albumin at a concentration of at least about 1 mg/mL. the compositions may be in the form of buffered solutions, such as for example, in a buffered solution comprising a sodium phosphate buffer at a concentration of about 10-50 mM.

In specific embodiments, the lysosomal storage disorder is MPS 1 and the enzyme is recombinant iduronidase administered intrathecally in an amount of about 0.5 µg to about 20 mg per kilogram of body weight. In specific embodiments, the amount is about 0.5 µg to about 0.5 mg per kilogram of body weight. More particularly, it is contemplated that the recombinant iduronidase is administered in a dosage of about 1.0 µg to 100 µg, 2.0 µg to 50 µg, or 10 µg to 100 µg per kilogram of body weight. These are merely exemplary amounts of iduronidase and those of skill in the art will understand that these doses may be varied depending on age of the subject, size of the subject, stage of the disease and the like. In preferred embodiments, the recombinant iduronidase is administered in a dosage of about 1.0 µg to 15 mg, 2.0 µg to 10 mg, or 10 µg to 5 mg.

The enzyme for the replacement therapy may be prepared from any source commonly used for the preparation of such enzymes. In certain embodiments, the enzyme is iduronidase that is secreted and purified from mammalian cells in culture transfected with a DNA sequence encoding human iduronidase.

The enzyme delivered in the intrathecal methods of treatment of the present invention may be administered through any convenient route commonly used for intrathecal administration. For example, the intrathecal administration may be via a slow infusion of at least 0.5 mg/kg of the formulation for about an hour. However, it should be understood that the dosage may vary from about 0.01 mg/15-20 kg body weight of the subject to about 10 mg/15-20 kg body weight of the subject over similar infusion rates. Advantageously, administering the intrathecal enzyme replacement therapy results in the normalization of lysosomal storage granules in the neuronal and/or meningeal tissue of the subjects as discussed above. In particularly preferred embodiments, it is contemplated that the deposition of storage granules is ameliorated from neuronal and glial tissue, thereby alleviating the developmental delay and regression seen in individuals suffering with lysosomal storage disease. Other preferred embodiments results in the normalization of lysosomal storage granules in the cerebral meninges near the arachnoid granulation, the presence of which in lysosomal storage disease result in high pressure hydrocephalus. Therefore, the methods of the invention are directed to the treatment of such high pressure hydrocephalus associated with lysosomal storage disease. The methods of the invention also may be used in treating spinal cord compression that results from the presence of lysosomal storage granules in the cervical meninges near the cord at C1-C5 or elsewhere in the spinal cord. The methods of the invention also are directed to the treatment of cysts that are caused by the perivascular storage of lysosomal storage granules around the vessels of the brain.

In other embodiments, the therapy also may advantageously result in normalization of liver volume and urinary glycosaminoglycan excretion, reduction in spleen size and apnea/hypopnea events, increase in height and growth velocity in prepubertal subjects, increase in shoulder flexion and elbow and knee extension, and reduction in tricuspid regurgitation or pulmonic regurgitation. For methods of monitoring such effects, those of skill in the art are specifically referred to Example 5 of U.S. Pat. No. 6,585,971, which is incorporated herein by reference specifically for teachings of Example 5, and more generally for teaching methods and compositions of formulating recombinant iduronidase.

In preferred embodiments, the therapeutic administering in the present application involves administration of human recombinant α-L-iduronidase, which reduces lysosomal storage in at least the brain tissue of the individual having the lysosomal storage disease. In those preferred aspects of the invention in which iduronidase is being administered intrathecally into the CSF, the composition being delivered comprises about 1 mg iduronidase/20 kg of body weight of the mammal being treated for MPS. In particular embodiments, the above dose is delivered to 15 cc CSF. At such a concentration it is contemplated that the enzyme concentration will be 18,000 units per ml of CSF. It should be understood that the aforementioned dosage is merely an exemplary dosage and those of skill in the art will understand that this dosage may be varied.

The intrathecal administration of the present invention may comprise introducing the pharmaceutical composition into a cerebral ventricle. Alternatively, the intrathecal administration may comprise introducing the pharmaceutical composition into the lumbar area. In yet another alternative, the intrathecal administration comprises introducing the pharmaceutical composition into the cisterna magna. Any such administration is preferably via a bolus injection. Depending on the severity of the symptoms and the responsiveness of the subject to the therapy, the such a bolus injection may be administered once per week, once per month, once every two months, once every three months, once every 6 months or annually. In other embodiments, the intrathecal administration is achieved by use of an infusion pump. The pharmaceutical could of course be intrathecally administered continually over a period of at least several days or alternatively, the intrathecal administration is continually over a period of at least four weeks. Of course, where the administration is via continuous infusion, the rate of dose administration of the enzyme replacement therapy may be greatly reduced as compared to the bolus injection administration.

In certain embodiments, the therapeutic regimens may be such that the intrathecal administration is combined with systemic administration of the pharmaceutical composition comprising said enzyme that is deficient in the disease in combination. In preferred such embodiments, the intrathecal administration may be performed on a monthly basis although other time intervals between administration also are contemplated. Preferably, the systemic administration in such combined administration regimens is intravenous administration. In specific embodiments, the methods of the invention contemplate treatment of a lysosomal storage disease by administering an enzyme such as rh-IDU intrathecally to effect delivery into the CNS and systemically to ameliorate the effects of the lysosomal storage disease in non-CNS sites. For example, in specific embodiments, the rh-IDU is administered intrathecally on a monthly basis and intravenously on a fortnightly, weekly, daily, or every other day basis. In certain embodiments, the subject may be tolerized to the intrathecal and/or rh-IDU administration using an immunosuppressive tolerization regimen prior to initiation of the therapeutic regimen.

The methods of the present invention are preferably for the therapeutic intervention of a human suffering for a lysosomal storage disease.

In preferred embodiments of the invention, the enzyme being delivered to the cerebrospinal fluid naturally comprises or has been engineered to comprise a component that allows the uptake of the enzyme by a high affinity receptor. For example, the enzyme comprises or has been engineered to comprise a moiety that allows said enzyme to bind to a receptor selected from a mannose-6-phosphate receptor, melanotransferrin receptor, and LRP receptor or any other receptor that is ubiquitously expressed on the surface of brain cells. In preferred embodiments, the enzyme comprises mannose-6-phosphate moieties that allow the enzyme to be taken up by a cell that expresses a mannose-6-phosphate receptor. In an alternative embodiment, the enzyme naturally binds, or has been engineered to possess GAG binding capacity. In an alternative embodiment, the enzyme comprises p97, RAP, transferrin or IGF2.

In certain aspects of the invention, the subjects being treated with enzyme replacement therapy for lysosome storage disease are rendered tolerant to such therapy using tolerization regimens.

In certain embodiments of the invention, the enzyme used for the enzyme replacement therapy in the lysosomal storage disease is one which naturally comprises, or is fused to, a moiety that facilitates the high uptake of the enzyme. In preferred embodiments, such an enzyme is iduronidase, whether recombinant or wild-type. The moiety that facilitates uptake of the enzyme may be any moiety such as a binding partner of a ligand or receptor expressed on the surface of the cell to be targeted for the therapy. In particularly preferred embodiments, the moiety is selected from the group consisting is a mannose-6-phosphate residue, a RAP polypeptide, and a p97 polypeptide. Other aspects of the present invention define methods which further comprise inducing antigen specific tolerance prior to the enzyme replacement therapy. Such induction of tolerance to the therapy may employ administration of an immunosuppressive agent, such as e.g., cyclosporine either alone or in combination with an agent such as azathioprine, which may have antiproliferative and/or co-stimulatory signal blocking effects.

Specific embodiments of the present invention contemplate methods of promoting the breakdown of glycosaminoglycan (GAG) in a brain cell of a subject having lysosomal storage disease, the method comprising intrathecally administering to the subject a pharmaceutical composition comprising an enzyme deficient in the lysosomal storage disease in an amount effective to reduce the amount of GAG present in the brain cell as compared to the amount of GAG present in the cell prior to the administration.

In specific embodiments throughout the present specification it should be understood that the methods of the invention may be used to reduce GAG storage and/or promote GAG breakdown in any brain cell that has an abnormal storage of GAG. The brain cells may be neuron, neuroglia, or ependymal cells. In specific embodiments, the brain cell may be selected from at least one of the group consisting of neurons, glial cells, microglial cells, astrocytes, oligodendroglial cells, perivascular cells, perithelial cells, meningeal cells, ependymal cells, arachnoid granulation cells, arachnoid membranes, dura mater, pia mater and choroid plexus cells. In preferred embodiments, the brain cell is a meningeal cell. It is contemplated that in certain embodiments, the subject has high pressure hydrocephalus and the administering reduces the amount of CSF fluid in the meningeal tissue of the subject. In other embodiments, it is contemplated that the subject has spinal cord compression and the administering reduces or otherwise alleviates the symptoms of said compression. In preferred embodiments, the therapeutic methods of the invention reduce the number of lysosomal storage granules in the cell as compared to the number of lysosomal storage granules present in a similar cell in the absence of the intrathecal administration.

Another embodiment of the invention contemplates a method of decreasing meningeal swelling in a subject having a lysosomal storage disease the method comprising intrathecally administering to the subject a pharmaceutical composition comprising an enzyme deficient in the lysosomal storage disease in an amount effective to decrease meningeal inflammation of the subject as compared to the size of the meninges of the subject prior to the administration. The subject may be a human subject.

Other beneficial aspects of the invention contemplate methods of decreasing spinal cord compression in a subject suffering from a lysosomal storage disease the method comprising intrathecally administering to the subject a pharmaceutical composition comprising an enzyme deficient in the lysosomal storage disease in an amount effective to decrease meningeal inflammation of the subject as compared to the size of the meninges of the subject prior to the administration. In these and other methods of the invention, the motor skills of the subject are preferably improved with the administration of the pharmaceutical composition as compared to the motor skills of the animal prior to the administration of the pharmaceutical composition.

The foregoing paragraphs are not intended to define every aspect of the invention, and additional aspects are described in other sections, such as the Detailed Description.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Although the applicants invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicants reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 10A shows GAG levels in brain were reduced to normal with treatment (*p=0.003). FIG. 10B shows GAG levels in spinal cord were reduced with treatment (p=0.22). FIG. 10C shows GAG levels in spinal meninges were reduced with treatment (*p=0.02).

DETAILED DESCRIPTION OF THE INVENTION

Figure 1:
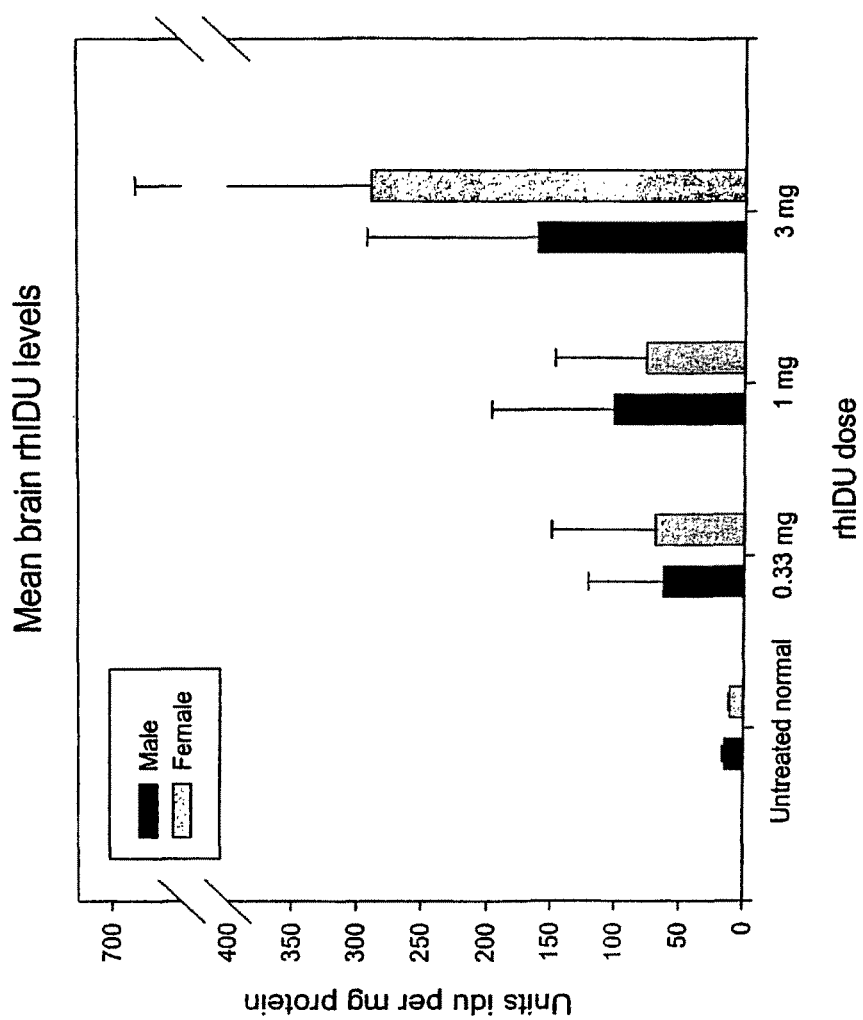
FIG. 1 describes enzyme levels in brain of canine subjects after intrathecal injection.

The present invention relates to methods for treating lysosomal storage disorders using intrathecal injection of enzymes deficient in the particular disorder being treated. The method can be coupled with a tolerance inducing regimen to provide a more effective treatment to subjects.

The present application is based on the discovery that intrathecal delivery of enzyme replacement therapy for lysosomal storage disorders results in sustained, long-term clinically useful therapeutic intervention of the central nervous system manifestations of such diseases. Properties of the enzyme such as solubility and binding to substrates can have an impact on the penetration of the enzyme into brain tissue and traversal of the therapeutic agent across the CSF-brain interface.

Thus, for the first time, the present specification details the successful treatment of the lysosomal storage diseases within the brain and meninges using recombinant iduronidase, thereby showing for the first time that it is possible to treat the brain and meningeal disease in storage diseases such as MPS I. Given that peripheral enzyme therapy for MPS I was approved for human use in 2003, the present invention allows the immediate translation to the treatment of human MPS I patients in clinical trials using the same recombinant iduronidase compositions presently approved for peripheral therapy. This represents an important advance in the treatment of lysosomal storage diseases since brain manifestations of lysosomal storage diseases have, to date, been refractory to treatment. While many of the exemplary methods described herein are exemplified using studies performed on MPS I, it is contemplated that the present findings may be extended to the treatment of other lysosomal storage disorders for which enzyme therapies are currently in development.

In particular embodiments, the instant specification details for the first time that the enzyme iduronidase can penetrate the brain better than other enzymes that have previously been attempted. In particular preferred embodiments, iduronidase is used to treat MPS disorders. Intrathecal administration of iduronidase is contemplated due to the ability of this enzyme to bind GAG in brain tissue, which may provide a binding site to pull the enzyme into the tissue fluid space. The presence of mannose-6-phosphate moieties on the iduronidase allows a high affinity uptake of the enzyme from the CSF, thereby allowing small concentrations of the enzyme in the CSF to have a clinically therapeutic effect. The fact that mannose-6-phosphate moieties bind to a high affinity receptor on the surface of nearly all cells allows even small amounts of iduronidase to be taken up by brain and meninges and be corrective of lysosomal storage disease at those sites.

Iduronidase demonstrates an extremely high affinity for its receptor with half maximal binding at concentration of approximately 1 nanomolar (12 units/ml) and moreover, given the half maximal correction of the defect at approximately 1 picomolar, the addition of even small amounts of enzyme into the CSF space would create an enormous gradient driving enzyme into the brain. In an exemplary treatment regimen, at a 1 mg dose in a 20 kg dog with 15 cc of CSF, the enzyme concentration in the CSF is predicted to be about 18,000 units/ml. This concentration is more than 1,000 fold above the concentration needed to observe uptake and 1,000,000 fold above the concentration required for half maximal correction. Therefore, even an inefficient process in which only 1% of the enzyme penetrates the brain would result in levels in the brain that are 10 times the uptake constant, a concentration that should drive efficient uptake and about 10,000 fold above the half maximal correction concentration. Given this easily achievable gradient, the effects of the properties of the enzyme on diffusion, and the low concentration needed for uptake and correction, it is demonstrated herein that iduronidase successfully treats symptoms of MPS I in vivo. One additional advantage in using intrathecal iduronidase therapy in treating MPS I is that MPS I disease enhances the permeability of the brain surface to enzyme therapy which makes intrathecal therapy an attractive method of treating MPS I.

The significance of the large concentration gradient resulting from intrathecal delivery of enzyme combined with the small but significant penetration of the enzyme into the brain could be sufficient to achieve therapeutic efficacy in any lysosomal storage disorder. The effect of this large concentration gradient generated by the high-uptake receptor binding property of iduronidase had not been appreciated prior to the present invention and is important in understanding how the brain can be force-fed enzyme across the ependymal layer and how a large number of enzymes may now be driven to diffuse across the blood brain barrier. Methods and compositions for achieving such correction with iduronidase, as well as other enzymes for lysosomal storage diseases are discussed in further detail herein below.

Definitions

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

The upper and lower limits of these smaller ranges may independently be included in the smaller ranges, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an" and "the" include plural referents unless the context clearly dictates otherwise.

By "lysosomal storage disease" is meant any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases are described in more detail below.

A "subject" is meant to include any animal that is to be treated using the methods of the invention. Preferably, the subject is a mammalian subject, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are included within the term "subject."

By "therapeutically effective," the present specification intends to denote any therapeutic benefit that arises as a result of the treatment methods of the present invention. For example, such an effect can be the beneficial effects that manifest in an appropriate target tissue, of the enzyme which is deficient or missing in the lysosomal disorder of interest, where such beneficial physiological effect is compared to that physiological parameter being measured in the absence of the enzyme replacement therapy. Such a therapeutic effect may be any reduction or elimination of one or more clinical or subclinical manifestations of the disease of interest. For example, a reduction in the number of storage vesicles (also termed storage granules), or elimination thereof, will provide a therapeutic benefit to the treated subject. Methods for detecting the presence of storage granules in a tissue of interest are well known in the art and described further below in the examples. Such methods entail microscopic examination of tissue sections. See, e.g., Vogler et al. (1990) *Am J Pathol* 136: 207-217. Moreover, reduction in the accumulation of substances due to the particular enzyme deficiency in question, will also confer a therapeutic benefit in the treated subject. Such substances may be readily detected using known assays. For example, MPS VII results in a build-up of un-degraded glycosaminoglycans (GAGs). GAG levels can be readily measured using methods developed by Farndale et al. (Farndale et al. (1982) *Con Tissue Res* 9: 247-248) and Poorthuis et al. (Poorthuis et al. (1994) *Pediatr Res* 36: 187-193).

Methods of the Invention

The present invention is directed to novel methods for the treatment of lysosomal storage diseases by providing intrathecal administration of enzymes defective or missing in such lysosomal storage disorders, thereby providing for the replacement of the defective or missing enzyme in the brain tissues of the subject being treated. Delivery to the brain target tissues is through an intrathecal route of administration. These methods effectively provide for the elimination or reduction of storage granules in the brain tissues of the treated subject.

Lysosomal storage diseases that may be treated using the methods of the invention include, but are not limited to, Gaucher's disease (see, e.g., Barranger et al. *Neurochemical Res.* (1999) 24:601-615 and NIH Technology Assessment Conference Statement, Feb. 27, 1995-Mar. 1, 1995) including Types 1, 2 and 3, Fabry's disease (see, e.g., Takanaka et al. *Exp. Hem.* (1999) 27:1149-1159, Ziegler et al. *Hum. Gene Ther.* (1999) 10:1667-1682 and Takanaka et al. *Hum. Gene Ther.* (1999) 10:1931-1939), Tay-Sachs disease (see, e.g., Guidotti et al. *Hum. Mol. Gen.* (1999) 8:831-838 and Daly et al. *Proc. Natl. Acad. Sci. USA* (1999) 96:2296-2300), Neimann-Pick Disease, Types A, B and C, ornithine-δ-aminotransferase (OAT) deficiency (see, e.g., Jensen et al. *Hum. Gene Ther.* (1997) 8:2125-2132, Locrazza et al. *Gene Ther.* (1995) 2:22-28, Rivero et al. *Hum. Gene Ther.* (1994) 5:701-707), hereditary homocysteinemia (see, e.g., McGill et al. *Am. J. Med. Gen.* (1990) 36:45-52, Eikelboom et al. *Ann. Int. Med.* (1999) 131:363-365, Watanabe et al. *Proc. Nat'l Acad Sci. USA* (1995) 92:1585-1589.), Mannosidoses, Fucosidoses, Sialodosis, the Mucolipidoses, such as I-cell Disease (Mucolipidoses II) and Pseudo-Hurler Polydystrophy (Mucolipidoses III), Acid Lipase Deficiency, such as Wolman Disease and Cholesterol Ester Storage Disease, Sulfatide Lipidosis including Metachromatic Dystrophy and Multiple Sulfatase Deficiency, MPS I (Hurler's disease) (see e.g., Lutzko et al. *Hum. Gene Ther.* (1999) 10:1521-1532, Hartung et al. *Hum. Gene Ther.* (1999) 10:2163-2172), MPS II (Hunter syndrome) (see e.g., Rathmann et. al. *Am. J. Hum. Genet.* (1996) 59:1202-1209, Stronicek et al. *Transfusion* (1999) 39:343-350, Li et al. *J. Med. Genet.* (1999) 36:21-27), MPS III (Sanfilippo syndrome) (see e.g., Scott et al. *Nat. Genet.* (1995) 11:465-467, Jone et al. *J. Neuropath. Exp. Neur.* (1997) 56(10):1158-1167), MPS IV (Morquoi's syndrome) (see e.g., Nothover et al. *J. Inherit. Metab. Dis.* (1996) 19:357-365), MPS V (Scheie's syndrome) (see e.g., Dekaban et al. *Arch. Pathol. Lab. Med.* (1976) 100:231-245), MPS VI (Maroteaux-Lamy syndrome) (see e.g., Hershovitz et al. *J. Inherit. Metab. Dis.* (1999) 22:50-62, Villani et al. *Biochim. Biophys. Acta.* (1999) 1453:185-192, Yogalingam et al. *Biochinz. Biophys. Acta.* (1999) 1453:284-296), and MPS VII (Sly syndrome) (see, e.g. Watson et al. *Gene Ther.* (1998) 5:1642-1649, Elliger et al. *Gene Ther.* (1999) 6:1175-1178, Stein et al. *J. Virol.* (1999) 73 (4):3424-3429, Daly et al. *PNAS* (1999) 96:2296-2300, Daly et al. *Hum. Gene Ther.* (1999) 10:85-94); and Sandhoff disease.

A detailed review of the genetic etiology, clinical manifestations, and molecular biology of the lysosomal storage diseases are detailed in Scriver et al., eds., *The Metabolic and Molecular Basis of Inherited Disease*, 7th Ed., Vol. II, McGraw Hill, (1995). Thus, the enzymes deficient in the above diseases are known to those of skill in the art, some of these are exemplified in the Table below:

| Lysosomal Storage Disease | Protein deficiency |
|---|---|
| Mucopolysaccharidosis type I | L-Iduronidase |
| Mucopolysaccharidosis type II Hunter syndrome | Iduronate-2-sulfatase |
| Mucopolysaccharidosis type IIIA Sanfilippo syndrome | Heparan-N-sulfatase |
| Mucopolysaccharidosis type IIIB Sanfilippo syndrome | α-N-Acetylglucosaminidase |
| Mucopolysaccharidosis type IIIC Sanfilippo syndrome | AcetylCoA: N-acetyltransferase |
| Mucopolysaccharidosis type IIID Sanfilippo syndrome | N-Acetylglucosamine 6-sulfatase |
| Mucopolysaccharidosis type IVA Morquio syndrome | Galactose 6-sulfatase |
| Mucopolysaccharidosis type IVB Morquio syndrome | β-Galactosidase |
| Mucopolysaccharidosis type VI | N-Acetylgalactosamine 4-sulfatase |
| Mucopolysaccharidosis type VII Sly syndrome | β-Glucuronidase |
| Mucopolysaccharidosis type IX | hyaluronoglucosaminidase |
| Aspartylglucosaminuria | Aspartylglucosaminidase |
| Cholesterol ester storage disease/Wolman disease | Acid lipase |
| Cystinosis | Cystine transporter |
| Danon disease | Lamp-2 |
| Fabry disease | α-Galactosidase A |
| Farber Lipogranulomatosis/Farber disease | Acid ceramidase |
| Fucosidosis | α-L-Fucosidase |
| Galactosialidosis types I/II | Protective protein |
| Gaucher disease types I/IIII Gaucher disease | Glucocerebrosidase (β-glucosidase) |
| Globoid cell leukodystrophy/Krabbe disease | Galactocerebrosidase |
| Glycogen storage disease II/Pompe disease | α-Glucosidase |
| GM1-Gangliosidosis types I/II/III | β-Galactosidase |
| GM2-Gangliosidosis type I/Tay Sachs disease | β-Hexosaminidase A |
| GM2-Gangliosidosis type II Sandhoff disease | β-Hexosaminidase A |
| GM2-Gangliosidosis | GM2-activator deficiency |
| α-Mannosidosis types I/II | α-D-Mannosidase |
| β-Mannosidosis | β-D-Mannosidase |
| Metachromatic leukodystrophy | Arylsulfatase A |
| Metachromatic leukodystrophy | Saposin B |
| Mucolipidosis type I/Sialidosis types I/II | Neuraminidase |
| Mucolipidosis types II/III I-cell disease | Phosphotransferase |
| Mucolipidosis type IIIC pseudo-Hurler polydystrophy | Phosphotransferase γ-subunit |
| Multiple sulfatase deficiency | Multiple sulfatases |
| Neuronal Ceroid Lipofuscinosis, CLN1 Batten disease | Palmitoyl protein thioesterase |
| Neuronal Ceroid Lipofuscinosis, CLN2 Batten disease | Tripeptidyl peptidase I |

| Lysosomal Storage Disease | Protein deficiency |
| --- | --- |
| Niemann-Pick disease types A/B Niemann-Pick disease | Acid sphingomyelinase |
| Niemann-Pick disease type C1 Niemann-Pick disease | Cholesterol trafficking |
| Niemann-Pick disease type C2 Niemann-Pick disease | Cholesterol trafficking |
| Pycnodysostosis | Cathepsin K |
| Schindler disease types I/II Schindler disease | α-Galactosidase B |
| Sialic acid storage disease | sialic acid transporter |

Thus, the lysosomal storage diseases that can be treated or prevented using the methods of the present invention include, but are not limited to, Mucopolysaccharidosis I (MPS I), MPS II, MPS IILN, MPS MB, Metachromatic Leukodystrophy (MLD), Krabbe, Pompe, Ceroid Lipofuscinosis, Tay-Sachs, Niemann-Pick A and B, and other lysosomal diseases as listed above. In particularly preferred embodiments, the enzyme is a lysosomal storage enzyme, such as α-L-iduronidase, iduronate-2-sulfatase, heparan N-sulfatase, α-N-acetylglucosaminidase, arylsulfatase A, galactosylceramidase, acid-alpha-glucosidase, tripeptidyl peptidase, hexosaminidase alpha, acid sphingomyelinase, α-galactosidase, or any other lysosomal storage enzyme.

In even more preferred embodiments, the disease to be treated is MPS I and the enzyme being replaced is iduronidase. Those of skill in the art are aware of compositions of comprising iduronidase, see for example, U.S. Pat. Nos. 6,585,971; 6,569,661; 6,524,835; 6,426,208; 6,238,662; 6,149,909. Each of the aforementioned patents is incorporated herein by reference as providing teachings of the iduronidase compositions that may be used in the methods of the invention. Iduronidase also is available commercially as ALDURAZYME™. The iduronidase may be naturally occurring iduronidase that has been isolated from an animal source or alternatively, may be recombinantly produced iduronidase, as produced according to exemplary methods described in the above-referenced patents. In certain embodiments, the iduronidase may be produced recombinantly in mammalian cells (e.g., as described in the above patents) or plant cells (e.g., as described in U.S. Pat. No. 5,929,304.)

In preferred embodiments, the methods of the invention reduce lysosomal storage granules in the meningeal and/or neuronal tissue of an individual manifesting lysosomal storage disease. In one sense, therefore, the invention comprises methods of reducing the size of meningeal and/or neuronal tissue of a subject having lysosomal storage disease, the method comprising intrathecally administering to the subject a pharmaceutical composition comprising an enzyme that is deficient in the lysosomal storage disease. In other embodiments, the invention also is directed to reducing lysosomal storage disease-associated high pressure hydrocephalus in a subject by providing to the subject an intrathecal administration of a pharmaceutical composition comprising an enzyme deficient in the lysosomal storage disease. Preferably, the enzyme is iduronidase. A therapeutically effective amount of iduronidase in these contexts is any amount of iduronidase that produces a detectable decrease in lysosomal storage granules, decreases meningeal and/or neuronal mass, reduces swelling associated with CSF present in the meninges of individual suffering from lysosomal disorder associated hydrocephalus and the like. Methods of determining whether the meninges of a subject are swollen are well known to those of skill in the art, and may include, for example, CAT scans.

In particular embodiments, the intrathecal administration discussed herein is used for the treatment of symptoms that result from lysosomal storage granules in neuronal, glial or other brain tissues of an animal. Such storage granules manifests in developmental delay and/or regression in development of the subject suffering from the disease. These symptoms and alleviation thereof with the treatment methods contemplated herein may be clinically assessed, for example using Bayley's Scales of Infant Development II, which includes monitoring a motor and developmental quotient. Development also may be assessed by monitoring language or other intellectual and motor developments. Evoked potential tests such as auditory or other evoked potential testing also may be used to assess the effects of the therapy on developmental delay and/or regression.

Other embodiments of the invention contemplate treatment of high pressure hydrocephalus caused by the presence of storage granules in the cerebral meninges near the arachnoid granulations. Such treatment may be monitored and assessed using art-recognized methods for determining CSF pressure via lumbar puncture and/or via an intraventricular catheter. Any release or reduction in the CSF pressure as a result of the therapeutic regimens of the present invention will be considered to be a therapeutic benefit of the present invention.

Treatment methods of the invention also are directed to ameliorating the effects of lysosomal storage in the cervical meninges near the cord at C1-C5 or elsewhere along the cord. Such storage results in symptoms associated with high pressure of CSF and also other symptoms associated with spinal cord compression. The storage results in progressive compressive spinal cord compression with lower extremity weakness, loss of bowel and bladder control and sensory deficits. Such symptoms may be monitored using e.g., neurological examination for abnormal Babinski's reflexes, deep tendon reflexes, motor function or sensation. Neurophysiological deficits of spinal cord compression may be assessed using somatosensory evoked potentials. Alternatively, magnetic resonance imaging with or without a contrast agent may be used to identify the anatomic location of compression as well as an evaluation of edema or other indicia of cord injury at the site of compression. The high pressure exerted by the CSF will lead to physiological manifestations such as headache, edema and the like. Any reduction in the pressure exerted by CSF, reduction in edema, or any improvement in the neurophysiological deficits, tendon reflexes, motor function or sensation observed as a result of the administration of the therapeutic regimen will be considered to be a therapeutically beneficial effect of the methods of the present invention. The subject may particularly be monitored for any level of improvement in lower extremity weakness, bowel and bladder control and sensory deficits associated with spinal cord compression.

Perivascular storage of lysosomal storage granules around the vessels of the brain may produce cysts. Such cysts and the effectiveness of the therapeutic regimens of the present application against such cysts may also be assessed using MRI scans to determine the size and number of such cysts. Any reduction in size and/or number of the cysts will be considered to be a therapeutically beneficial effect of the methods of the present invention.

Any release or reduction in the CSF pressure, reduction in the size and/or number of cysts or any other decrease in the symptoms caused by the presence of lysosomal storage granules as a result of the therapeutic regimens of the present invention will be considered to be a therapeutic benefit of the present invention. Such decreases are preferably in the order of at least 5% as compared to the levels of such symptoms prior to the administration. Of course, a greater decrease, e.g., 10%, 15%, 20%, 25%, 30%, 35%, 40%, 45% or more would be preferable. Most preferably, the symptoms are reduced/ameliorated to such an extent as to make the symptoms in subject indistinguishable from the same indicia observed in a normal healthy subject of like sex, age and physical characteristics.

Assessment of Methods in Model Animals

The methods of the present invention may be evaluated using models of lysosomal storage disease that are known to those of skill in the art. For example, a canine model of MPS I may be used as described in the examples herein below. Other models of MPS also may be used. Many pre-clinical studies rely on mouse models for a given disease. One such model is the MPS model described in example 1 of U.S. Pat. No. 6,582,692, which details crossing of $Gus^{mps/+}$ mice in the original C57BL/6 (B6) background (Jackson Laboratory, Bar Harbor, Me., USA) with the congenic strain B6Gusa (Pfister et al. (1982) *Biochem Genet.* 20: 519-535) to produce $Gus^{mps/a}$ progeny for a breeding colony in which both parents were always $Gus^{mps/a}$ and progeny carried mps/a, a/a or mps/mps allele combinations. The parameters for GUS activity may be monitored as described in that patent.

Yet another model that may be useful for evaluating the methods of the present invention is one exemplified in U.S. Pat. No. 6,002,067, which is transgenic mouse model for iduronidase deficiency. Of course, those of skill in the art also will be aware of other models that may be used in evaluating the methods of the present invention. Once the methods have been evaluated in such model animals, the methods are then readily scaled and adapted for the treatment of other mammalian subjects such as primates and preferably human subjects.

One of the most dramatic characteristics of MPS disease is the appearance of large, cytoplasmic, storage vacuoles apparent by microscopic examination of tissue sections (Vogler et al. (1990) *Am J Pathol* 136: 207-217). In one example using a MPS mouse model, MPS mice injected intrathecally with a composition comprising either iduronidase or saline alone are sacrificed 4 weeks after administration and examined histologically, as follows. Mice are killed by cervical dislocation and immediately perfused via the left ventricle, first with saline and then with 10% neutral buffered formalin. The fixed animals with exposed viscera are then immersed in formalin before histopathologic evaluation. Selected tissues are processed using routine techniques, embedded in paraffin, cut at approximately 5 microns, stained with hematoxylin and eosin, and examined microscopically. In particular, it will be desirable to perform such histopathologic evaluation on meningeal and/or neuronal cells of the animals.

Brain sections from control MPS animals should show moderate to severe, diffuse, cytoplasmic vacuolations in meninges and/or neuronal cells. Such cells from treated mice have a substantial reduction of storage vacuoles resulting in normal tissue architecture.

In order to assess the presence of storage granules in brain, mice are sacrificed by cervical dislocation, the brain was removed and one hemisphere was fixed in 10% neutral buffered formalin. 5 µM sections are stained with hematoxylin and eosin (H and E).

As discussed above, both neonatal and adult animals may be treated with intrathecal administration of iduronidase. In model mice, three-day old neonatal mice and e.g., adult mice of 7-13 weeks old at the time of injection can be treated with 0.01 µg to about 5 µg enzyme. It should be noted that dose is likely to the $1/1000^{th}$ the dose that required for a larger mammal such as a dog. For intrathecal administration to newborns, mice are anesthetized by inhalation of halothane, and iduronidase in 30 µl saline (with 2% dye) may be injected between the sixth lumbar and second sacral vertebrae using a 30-gauge needle. Successful introduction into the cerebrospinal fluid space is detected immediately as a green streak extending from the spinal column and diffusing into the brain. For intrathecal administration to adults, MPS mice are anesthetized with avertin (tribromoethanol) and a 1 cm incision is made through the skin parallel to the spine to make the positions of individual vertebrae visible. Iduronidase with 2% dye may then be injected between the last thoracic and second lumbar vertebrae.

At increasing times after this treatment, mice are sacrificed and tissues analyzed for iduronidase levels. Therapeutic levels of iduronidase enzyme are scored as any level which produced a detectable decrease in storage vacuoles. Of course, the above model studies are presented merely by way of example, with other exemplary model studies are described in the Examples herein below, these model studies may readily be modified without departing from the scope of the claimed invention.

Modification of Enzyme to Facilitate Improved Uptake

In the methods of the present invention, it may be preferably to ensure that the enzyme being administered to the subject through intrathecal administration is one which comprises a moiety that may be readily taken up by a high affinity uptake receptor on the surface of a brain cells. For example, such a receptor may be the mannose-6-phosphate receptor and the enzyme comprises up to about an average of about at least 20% bis-phosphorylated oligosaccharides per enzyme. In other embodiments, the enzyme may comprise 10%, 15%, 18%, 20%, 25%, 30%, 35%, 40%, 45% bis-phosphorylated oligosaccharides per enzyme. While such bis-phosphorylated oligosaccharides may be naturally present on the enzyme, it should be noted that the enzymes may be modified to possess such oligosaccharides. For example, those of skill in the art are aware of enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. Nos. 6,537,785, and 6,534,300, each incorporated herein by reference.

In other embodiments, the lysosomal enzymes for use in the present invention may be conjugated to a RAP and RAP polypeptides, which selectively bind to LRP receptors that may be present on brain cells. As such, these RAP molecules will serve to increase the transport of the lysosomal enzyme across the blood brain barrier and/or deliver agents to lysosomes of cells within the CNS. Methods and compositions for preparing enzyme compositions that comprise RAP moieties attached thereto are described in detail in U.S. patent application Ser. No. 10/206,448, filed on Jul. 25, 2002 and in U.S. patent application Ser. No. 10/600,862, filed Jun. 20, 2003, each incorporated herein by reference.

In still a further embodiment, those of skill in the art may employ a delivery of the enzyme conjugated to melanotransferrin (p97) as described in e.g., U.S. Pat. Nos. 6,455,494 and 5,981,194, each incorporated herein by reference. Of course the above agents that enhance the delivery and/or uptake of therapeutic agents to brain tissue are merely exemplary and those of skill in the art will be aware of other receptors, ligands or other agents that may be used in a similar context to deliver a therapeutic agent across the brain-CSF interface or even the BBB.

Combination Therapy to Tolerize Subject to Enzyme Replacement Therapy

It has been found that during administration of agents such as recombinant proteins and other therapeutic agents, a subject can mount an immune response against these agents, leading to the production of antibodies that bind and interfere with the therapeutic activity as well as cause acute or chronic immunologic reactions. This problem is most significant for therapeutics that are proteins because proteins are complex antigens and in many cases, the subject is immunologically naive to the antigens. Thus, in certain aspects of the present invention, it may be useful to render the subject receiving the therapeutic enzyme tolerant to the enzyme replacement therapy. In this context, the enzyme replacement therapy may be given to the subject as a combination therapy with a tolerizing regimen.

Co-owned, co-pending U.S. patent application Ser. No. 10/141,668 (incorporated herein by reference) discloses treatment of lysosomal storage disorders using immune tolerance induction. Briefly, use of such a tolerization regimen may be useful to prevent the subject mounting an immune response to the enzyme replacement therapy and thereby decreasing or otherwise rendering ineffective the potential beneficial effects of the enzyme replacement therapy.

In a preferred method, the invention contemplates reducing or preventing a clinically significant antigen-specific immune response to recombinant human α-L-iduronidase used to treat mucopolysaccharidosis I (MPS I), where the iduronidase is administered intrathecally. The method employs an initial 30-60 day regimen of a T-cell immunosuppressive agent such as cyclosporin A (CsA) and an antiproliferative agent, such as, azathioprine (Aza), combined with weekly intrathecal infusions of low doses of iduronidase. The typical strong IgG response to weekly infusions of iduronidase becomes greatly reduced or prevented using a 60 day regimen of immunosuppressive drugs, cyclosporin A (CsA) and azathioprine (Aza), combined with weekly intrathecal infusions of low doses of rhIDU. Using such tolerization regimens, it will be possible to render the subject tolerant to higher therapeutic doses of iduronidase for up to 6 months without an increase in antibody titer against the iduronidase, or indeed any other enzyme that could be used for enzyme replacement of a lysosomal storage disease. Such tolerization regimens have been described in U.S. patent application Ser. No. 10/141,668, specifically incorporated herein by reference.

Intrathecal Administration of the Pharmaceutically Acceptable Formulations

As discussed above, the present invention is based on surprising discoveries of the therapeutic efficacy of using intrathecal administration of enzyme replacement therapy for lysosomal storage disease. In one embodiment, the enzyme is administered by introduction into the central nervous system of the subject, e.g., into the cerebrospinal fluid of the subject. In certain aspects of the invention, the enzyme is introduced intrathecally, e.g., into the lumbar area, or the cistema magna or intraventricularly into a cerebral ventricle space.

Those of skill in the art are aware of devices that may be used to effect intrathecal administration of a therapeutic composition. For example, the therapy may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

As used herein, the term "intrathecal administration" is intended to include delivering a pharmaceutical composition directly into the cerebrospinal fluid of a subject, by techniques including lateral cerebroventricular injection through a burrhole or cisternal or lumbar puncture or the like (described in Lazorthes et al. *Advances in Drug Delivery Systems and Applications in Neurosurgery*, 143-192 and Omaya et al., Cancer Drug Delivery, 1: 169-179, the contents of which are incorporated herein by reference). The term "lumbar region" is intended to include the area between the third and fourth lumbar (lower back) vertebrae and, more inclusively, the L2-S1 region of the spine. The term "cisterna magna" is intended to include access to the space around and below the cerebellum via the opening between the skull and the top of the spine. The term "cerebral ventricle" is intended to include the cavities in the brain that are continuous with the central canal of the spinal cord. Administration of a pharmaceutical composition in accordance with the present invention to any of the above mentioned sites can be achieved by direct injection of the composition or by the use of infusion pumps. For injection, the composition of the invention can be formulated in liquid solutions, preferably in physiologically compatible buffers such as Hank's solution, Ringer's solution or phosphate buffer. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" is intended to include continual delivery of a pharmaceutical composition of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

The pharmaceutical formulation used in the method of the invention contains a therapeutically effective amount of an enzyme for use in enzyme replacement therapy of a lysosome storage disease. Such a therapeutically effective amount is any amount effective, at dosages and for periods of time necessary, to achieve the desired result. In preferred embodiments, the compositions comprises a therapeutically effective amount of iduronidase. A therapeutically effective amount of iduronidase may vary according to factors such as the disease state, age, and weight of the subject, and the ability of the enzyme (alone or in combination with one or more other agents) to elicit a desired response in the subject. Dosage regimens may be adjusted to provide the optimum therapeutic response. A therapeutically effective amount is also one in which any toxic or detrimental effects of the composition are outweighed by the therapeutically beneficial effects. A non-limiting range for a therapeutically effective concentration of iduronidase is 0.001 µg enzyme/ml to about 15 µg enzyme/ml. It is to be noted that dosage values may vary with the severity of the condition to be alleviated. It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

The enzyme composition is preferably in the form of an injectable unit dose. Examples of carriers or diluents usable for preparing such injectable doses include diluents such as water, ethyl alcohol, macrogol, propylene glycol, ethoxylated isostearyl alcohol, polyoxyisostearyl alcohol and polyoxyethylene sorbitan fatty acid esters, pH adjusting agents or buffers such as sodium citrate, sodium acetate and sodium phosphate, stabilizers such as sodium pyrosulfite, EDTA, thioglycolic acid and thiolactic acid, isotonic agents such as sodium chloride and glucose, local anesthetics such as procaine hydrochloride and lidocaine hydrochloride. Furthermore usual solubilizing agents and analgesics may be added. Injections can be prepared by adding such carriers to the enzyme or other active, following procedures well known to those of skill in the art. A thorough discussion of pharmaceutically acceptable excipients is available in REMINGTON'S PHARMACEUTICAL SCIENCES (Mack Pub. Co., N.J. 1991).

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

Kits for Use in the Methods of the Invention

The agents utilized in the methods of the invention may be provided in a kit, which kit may further include instructions for use. Such a kit will comprise an enzyme for use in the treatment of a lysosomal storage disease, usually in a dose and faun suitable for administration to the host. The kit will usually comprise a device for delivering the enzyme intrathecally. The kit may further comprise a T cell immunosuppressive agent, in a form suitable for administration, and may further include assay reagents for monitoring blood levels of the agent, and/or for determination of suppression of T cell activity. An anti-proliferative agent may also be included, in a form suitable for administration.

A kit may also provided for the conjugation of an antigen, particularly a polypeptide antigen, to a high uptake moiety, in order to generate a toleragenic composition. For example, a moiety such as a mannose 6 phosphate group, either conjugated to a linker suitable for linking sugars and polypeptides, as described above, may be provided. The high uptake moiety may also be provided in an unconjugated form, in combination with a suitable linker, and instructions for use.

Another kit may comprise instructions for the intrathecal administration of the therapeutic compositions of the present invention, in addition to the therapeutic compositions. In certain embodiments, the kits of the invention may comprise catheters or other devices for the intrathecal administration of the enzyme replacement therapy that are preloaded with the therapeutic compositions of the present invention. For example, catheters preloaded with 0.001 mg, 0.005 mg, 0.01 mg, 0.015 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg or more of iduronidase in a pharmaceutically acceptable formulation are specifically contemplated. Other enzymes for use in lysosomal storage diseases also may be similarly presented in pre-loaded catheters for intrathecal administration. Exemplary catheters may single use catheters that can be discarded after use. Alternatively, the preloaded catheters may be refillable and presented in kits that have appropriate amounts of the enzyme for refilling such catheters.

Additional aspects and details of the invention will be apparent from the following examples, which are intended to be illustrative rather than limiting.

EXAMPLE 1

Protocols for Assessing Direct Injection of the Brain with Recombinant Human Iduronidase Those of skill in the art also are aware of well-known canine models for lysosomal storage diseases. In one embodiment, MPS I canines are used to assess the efficacy of the methods of the present invention. For such determinations, it is desirable that normal canines and MPS I canines are assessed concurrently. The following example provides exemplary protocols for use in conjunction with the methods described herein.

In order to assess enzyme penetration in the brain of normal canines, normal beagle dogs (e.g., 2 initially planned, up to 4 possible) are prepared for anesthesia and sterility. An Ommaya reservoir or equivalent device is implanted with a ventricular catheter placed in the lateral ventricle. A CSF reservoir and lumbar catheter may also be implanted in the lumbar region. CSF is withdrawn to confirm patency. Enzyme administration and CSF sampling is performed at the lateral ventricle in one of the beagles. The system at the lumbar region in this beagle serves as a backup system in the event of irreversible problems occurs at the original site of access. The second beagle is set up to receive enzyme and CSF sampling at the lumbar region. The system at the lateral ventricle in this second beagle will serve as a backup system in the event of irreversible problems at the original site of access. The enzyme is administered at weekly injections for four weeks. PK studies of CSF clearance of iduronidase are assessed using a set of timed samplings at the first and last week of injection. All CSF samples obtained are analyzed for safety, PK and pharmacodynamics of enzyme penetration. In the event that complications arise while placing the ventricular system in the normal beagles, the methods of the present invention may be assessed using an administration system placed only in the lumbar region. Thus, enzyme administration and CSF sampling will occur at the lumbar regions only. At the termination of treatment, brain tissue may be collected to assess iduronidase activity using a validated assay. Brain tissue will also analyzed for storage using light microscopy and confocal immunofluorescence. Tissues both proximal and distal to the site of ventricular penetration may be assessed for enzyme penetration.

In order to determine the enzyme penetration in the model animals for lysosomal storage disease, the above protocol is repeated using MPS I canines.

To assess the response of the animals to the treatment, a variety of parameters may be monitored. To obtain a baseline assessment, it may be desirable to perform a clinical examination to assess, physical condition, vital signs and weight. This assessment should preferably be supplemented with clinical laboratory analyses to determine the Complete Blood Count (CBC) and Superchem profile and urinanalysis of the animals. Urine specimens should be analyses for the presence of glycosaminoglycans, serum analysis should be performed to assess the presence of anti iduronidase antibodies as this may have an affect on the amount of idurondase that should be administered. Plasma iduronidase activity also should be assessed. The baseline assessment also should include an analysis of the CSF for standard CSF lab analysis (cell count, protein, glucose and cytology), GAG, ELISA for anti-idu antibodies, and iduronidase analysis. The cells present in the CSF should be assessed for the presence of storage granules using a simple stain. These parameters should then be assessed periodically throughout the period of therapy. At the end of the analysis period, brain tissue may be obtained and analyzed further. Such analyses may include a brain biopsy to perform an iduronidase assay and tissue GAG levels. The pathology of MPS I animals may be assessed using light and electron microscopy, and confocal immunofluorescence using anti-iduronidase antibodies also may be performed.

The following is a discussion of the general methods used to perform the above-outlined assessments.

Clinical Examination: In order to assess the physical condition of the animals, a general physical examination should note the posture, activity, demeanor and general appearance, preferably on a daily basis throughout the course of the experiment the examination should note the vital signs of the animal (heart rate, body temperature, and respiratory rate), particularly after each injection. Growth may be assessed by periodically taking body weight measurements.

CSF and plasma α-L-iduronidase levels: Enzyme levels may be measured in the plasma and CSF just prior to enzyme administration to the CSF each week. CSF is obtained after sterile preparation of the CSF port and accessed with a sterile needle. The enzyme in blood samples is stabilized by adding $1/10^{th}$ volume of 100 mM NaPO4/Citrate pH 4.0 The enzyme is assayed for iduronidase using a validated assay with the artificial substrate 4-methylumbelliferyl-α-1-iduronide. Net fluorescence is determined by fluorometry at 365 nm excitation and 440 nm emissions. One unit of iduronidase is equivalent to the number of micromoles of substrate cleaved per minute at 37° C. in the conditions of the assay.

Brain tissue α-L-iduronidase: Enzyme levels may be measured in a biopsy specimen obtained. In the MPS canines, biopsies may be obtained prior to perfusion. A brain sample is snap frozen in a labeled vial in liquid nitrogen. After thawing, the specimen is weighed quickly and 3 vol of PAD (10 mM phosphate-buffer pH 5.8, 0.02% azide and 0.1 mM dithiothreitol)+0.1% Triton X-100. The tissue sample is ground in Dounce ground glass homogenizer by a minimum of 10 strokes while on ice and the homogenate cleared of large particles by spinning in a microfuge for a few seconds. The extract is stored by snap freezing. The enzyme is assayed for iduronidase using a validated assay with the artificial substrate 4-methylumbelliferyl-α-1-iduronide. Pilot assays should preferably be performed to determine the time of assay required and whether dilution is needed. Net fluorescence is determined by fluorometry at 365 nm excitation and 440 nm emissions. One unit of iduronidase is equivalent to the number of micromoles of substrate cleaved per minute at 37° C. in the conditions of the assay.

GAG Analyses: At the conclusion of the therapy, the dogs may be euthanized and brain tissue samples collected by biopsy and quick frozen with liquid nitrogen for subsequent tissue glycosaminoglycan analysis. For tissue GAG analysis, sulfated glysocaminoglycans will be assayed using a modification of the Alcian Blue method of Bjornsson as published (Kalckis et al., *Biochem Mol. Med.* 1996; 58(2):156-67). The GAG quantities can be determined by comparison to standards of dermatan sulfate. Urinary and CSF GAG quantification is completed in a method nearly identical to that used to quantify tissue GAG content performed on urine and CSF samples.

CSF Storage: Cellular debris from the CSF can be identified using a simple stain and the cells readily assessed for GAG storage.

CSF Pharmacokinetics Studies: Pharmacokinetic studies may be completed on each treated dog during the first and last weeks of enzyme replacement therapy to monitor α-L-iduronidase clearance from the CSF following an infusion. After administration of enzyme to the CSF via the ventricular port, samples are drawn from the same site of enzyme administration at 1, 2, 4 hours. The samples are withdrawn and prepared as in the section on CSF samples. Data is plotted as time versus CSF iduronidase activity. Half-life of iduronidase in the circulation can be determined.

CBC, Superchem Profile and Urinalysis: Blood samples are collected every two weeks for a CBC and superchem profile. Urinalysis with reagent strips is also performed every other week on a fresh urine sample to monitor items such as proteinuria and hematuria.

ELISA for α-L-iduronidase specific antibodies: Serum samples are collected and frozen at −20° C. for subsequent antibody analysis. Antibodies specific for iduronidase are detected by standard ELISA protocol using goat anti-dog IgG labeled with alkaline phosphatase as the secondary antibody. Antibodies in the CSF are determined by the same method though it is expected that a smaller dilution may be needed.

Enzyme Composition Delivered: Recombinant human α-L-iduronidase is supplied by BioMarin Pharmaceutical from bulk lots that may or may not be released for human use. The enzyme should preferably meet all relevant specifications required for enzyme therapy and safe administration including passing potency, activity, sterility, and endotoxin levels. The dosage form consists of enzyme at 100,000 u/ml in formulation buffer (100 mM NaPO4, pH 5.8, 150 mM NaCl at pH 5.3-5.8).

Placement of the indwelling ventricular device: Procedures have been described for sampling via the ventricular system (McCully et al; Poplack et al; Moir and Dow et al; Kusumi and Plouffe; Haslberger and Gaab). Some of these also involve trauma to the brain and do not permit precise positioning of the delivery system. We will use a technique that permits an investigator to obtain multiple sterile CSF samples or administer multiple injections into the CSF of unanaesthetized animals that are restrained with a minimal dose of tranquilizers. The procedure involves the placement of an indwelling catheter into the lateral ventricles as well as the intrathecal space of lumbar region of the spine.

In the examples discussed herein, the animals, e.g., two normal, male, adult laboratory-reared Beagle dogs and two, male dogs with mucopolysaccharidosis I are used. Dogs are atropinized (0.045 mg/kg), and anesthesia is induced with intravenous Propofol (1-6 mg/kg) titrated to effect. The dogs are intubated and maintained on Isoflurane anesthesia with oxygen, and placed on a heating pad during surgery to maintain normal body temperature. Normal saline will be administered for fluid maintenance. Antibiotics may be administered prior to and during surgery to prevent infection.

The dog is placed on its ventrum with the head supported to ensure that the airway remains patent. The occiput and dorsal midline is clipped, surgically scrubbed and draped. Sterile technique and loupe magnification is used throughout the procedure. The appropriate length of the catheter is predetermined by measuring the thickness of the first two cervical vertebrae (C1 and C2), the distance from C2 and the distance to the cistern. The volume of fluid necessary to fill the volume of the catheter and reservoir (dead space) is calculated.

The skin is incised on the midline from the occipital prominence along the dorsal midline to expose the foramen magnum, the junction of C1 and the occiput, and the atlanto-occipital membrane. The subcutaneous muscles are sharply dissected and the ligamentum nuchae are divided. Using an air drill and scalpel a small keyhole is created in the posteruir ekenebts of C1 and a 2 mm horizontal slit is made in the dura to enter the cisterna magna, Using a surgical hook, the pre-measured length of a perforated Spetzler lumbar silicone catheter containing a stylet is threaded into the ventricle space and CSF is withdrawn to confirm patency. The catheter is anchored to the muscle near the reservoir. Hemostasis is accomplished with a bipolar electrocautery unit. A subcutaneous subgaleal pocket is created in the occipital area to accommodate the Ommaya reservoir. The reservoir is secured with non-absorbable suture to the occipital pericranium. The remaining external portion of the catheter is extended to the subcutaneous pocket, and a metal step-down connector is used to attach the catheter to the Ommaya reservoir and silk suture may be used to ensure the connection.

To determine the patency of the catheter, a small quantity of CSF, which just exceeds the combined dead space of the catheter and reservoir, is gently withdrawn using a 25-gauge ⅝-inch needle affixed to a 1 cc syringe. The reservoir is secured with non-absorbable sutures to the occipital pericranium. The system is examined for leakage, and the operative site closed in anatomical layers with interrupted 3.0 Vicryl sutures. The skin is then closed with nylon sutures.

Withdrawal of CSF or injections into the reservoir are done using sterile technique (surgical scrub of the skin and sterile gloves) with a 25 gauge ⅝ inch needle affixed to a 1 cc syringe. The CSF should be withdrawn gently and steadily.

Postoperatively, the dog is monitored and intravenous fluids are administered as needed until it is able to stand, eat and drink. The analgesic buprenorphine (0.01 mg/kg SQ at 12 hour internals) may be administered as necessary to relieve discomfort. Antibiotics may be administered 10 days postoperatively. The dog should be clinically examined daily.

To maintain patency, the system should be flushed weekly. This will allow sampling of CSF and administration of enzyme. To administer the enzyme or withdraw CSF, the dogs are restrained with 0.1 mg/kg of acepromazine and increased as needed. The skin over the reservoir is clipped and surgically scrubbed. Wearing sterile gloves, the location of the reservoir behind the ear is determined, and entered using a 25-gauge needle attached to a 1 ml syringe. Particular care should be taken to enter the dome of the reservoir a few millimeters away from the area of the skin puncture to minimize exogenous contamination. A volume of CSF equal to the volume of the catheter plus the reservoir is removed and discarded by removing the syringe and expelling its contents; then, the desired amount of CSF is withdrawn or the enzyme administered into the reservoir. When enzyme is administered (18,000 units/mL CSF), it is preferable to "chase" the enzyme with a volume of physiologic saline equivalent to the dead space volume of the catheter and reservoir. This ensures that the enzyme is administered directly into the ventricular system. CSF sampling and enzyme administration is continued as discussed above following installation of the catheter.

For tissue analysis, after eight weeks of enzyme treatment the dogs are deeply anesthetized (loss of toe pinch and eyelid reflexes) with an overdose of sodium pentobarbital, and flushed intracardially with heparinized saline. A small cranial opening is made in the frontal area and a small section of brain is removed. The dog is then perfused intracardially with 4% paraformaldehyde.

Throughout the above treatment protocols, the canines should be monitored closely for signs of an anaphylactic reaction during and immediately after enzyme administration. Signs of a reaction may include behavioral changes, such as restlessness, irritability, or extreme stillness, as well as vomiting, bowel movements, and loss of color in the mucous membranes. If any of these symptoms or other adverse symptoms occur, the administration should be stopped, diphenhydramine may be administered, followed by a saline drip and administration of oxygen. The infusion may be continued when the reaction subsides.

Canines are also monitored for infection due to the exteriorized catheter and are treated by appropriate measures (catheter removal, local control of infection, systemic antibiotics). If an infection occurs, such as ventriculitis, enzyme treatments will be postponed until the infections has been adequately treated with gentamicin.

The following examples describe the results of studies performed on the intrathecal administration of iduronidase to MPS I model animals using some or all of the methods described in the above example.

EXAMPLE 2

Enzyme Administered Via Intraventricular Injection Penetrates Blood Brain Barrier and is Detected in Brain Tissue Administration of enzymes directly to the site of lysosomal storage induced damage in the brains of subjects with lysosomal storage disorder has proven difficult to this point. The large enzyme complexes necessary to treat these diseases typically cannot penetrate the blood brain barrier. To determine an effective method for drawing these enzymes across the brain-CSF interface, two routes of enzyme administration were tested in a rat and canine model of the lysosomal storage disorder MPS I.

To administer enzyme intraventricularly, rats were injected in the lateral ventricle, using sterotactic guidance, with either 5-10 μl of recombinant human iduronidase (rhIDU) or control protein. Animals were sacrificed 24 hours after injection and brain sections obtained.

Brain sections were analyzed for the presence of rhIDU using confocal microscopy with anti-iduronidase antibodies. Immunohistochemical analysis showed that the injected enzyme is taken up by brain neurons, and further that the iduronidase is localized to the lysosomes in the neuronal cells. Anti-IDU staining indicates that the enzyme penetrates the brain tissue for several millimeters, but there is a decreasing gradient of enzyme, meaning that the farther away from the injection site the less enzyme is detected in the brain. The staining also indicated that the half-life of the enzyme was approximately 7 days.

Brain sections were also analyzed for rhIDU activity.

Analysis of enzyme levels in brain of subjects after intrathecal injection (FIG. 1) demonstrated that animals given 0.33 mg of iduronidase show 5-fold increase of enzyme in the brain compared to control animals (mean, 65±28 Units/mg protein), animals receiving 1 mg/injection showed a 7-fold increase in enzyme (mean enzyme levels of 89±62 U/mg), while animals receiving 3 mg enzyme/injection showed a 17-fold increase in enzyme levels, with a mean iduronidase level of approximately 224±32 U/mg. Thus, increasing the dosage of iduronidase administered to a subject increases the level of iduronidase in the detected in the brain.

In similar experiments in which the 6 dogs were treated with low (0.46 mg/injection), medium (1.08/1.38 mg/injection) and high (4.14 mg/injection) of rh-iduronidase doses administered via the cisterna magna once per week for four weeks and assayed the iduronidase content of the brain at 48 hours after the last dose (see Table 1 for specific doses). The two intrathecally-treated dogs at each dose level were compared with the iduronidase enzyme levels in two untreated normal dogs. The IT-treated dogs had 5.6, 7.5 and 18.9-fold the enzyme levels of untreated or vehicle-treated animals for the low, medium, and high doses, respectively (Table 1). Given that the corrective concentration of enzyme is as low as 2-5% of normal, these levels represented concentrations very far above the required corrective levels of enzyme.

TABLE 1

Dose-response effects of rhIDU administered IT to normal dogs

| Weekly Dose of IT rhIDU (mg) | Total Brain[¥] | Fold Normal | Surface Brain[¥] | Fold Normal | Deep Brain* | Fold Normal |
|---|---|---|---|---|---|---|
| Untreated/Placebo-treated Normal | 11.9 ± 1.95 [10.1-15.0] | 1 | ND | 1 | ND | 1 |
| Low (0.46) | 66.4 ± 4.07 [63.5, 69.3] | 5.6 $p = 0.0001$* | 101 ± 19.5 [87.5, 115] | 8.5 $p = 0.0001$* | 31.8 ± 3.75 [29.1, 34.4] | 2.7 $p = 0.0002$* |
| Medium (1.08/1.38) | 89.0 ± 18.2 [76.0, 102] | 7.5 $p = 0.0001$* | 121 ± 43.4 [90.5, 152] | 10.2 $p = 0.0011$* | 52.3 ± 0.64 [51.8, 52.7] | 4.4 $p < 0.0001$* |
| High (4.14) | 225 ± 89.5 [161, 288] | 18.9 $p = 0.0014$* | 355 ± 198 [214, 495] | 29.8 $p = 0.0057$* | 70.6 ± 14.1 [60.6, 80.5] | 5.9 $p = 0.0001$* |

Iduronidase levels are calculated from mean values for each region for each dog sacrificed. Means of the means for each animal ± standard deviation are shown. N = 5 for the untreated group and N = 2 for each dosage group.
[¥]Iduronidase levels are expressed in units of iduronidase per mg protein.
*Statistically significant.
ND is not done.

EXAMPLE 3

Enzyme Administered Via Intrathecal Injection Penetrates and is Detected in Brain Tissue To determine whether intrathecal injection of enzyme involved in lysosomal storage disorders could cross the blood brain barrier as effectively, or more effectively, than intraventricular injection, intrathecal injection into the CSF was performed in canine subjects.

Animals (n=2/group) were administered 1 cc rh-iduronidase, with a total protein content of 0.33 mg, 1 mg, or 3 mg, via injection into the cisterna magna. This protocol was repeated weekly for a total of four weeks. Brain sections were taken for analysis 48 hours after the last injection. For analysis, the right half of the brain was sliced cranially and alternate sections analyzed for enzyme activity, immunohistochemical localization of enzyme in brain and glycosaminoglycan content in brain sections. The left half of the brain was sliced coronally and assayed by light microscopy and electron microscopy.

Figure 2:
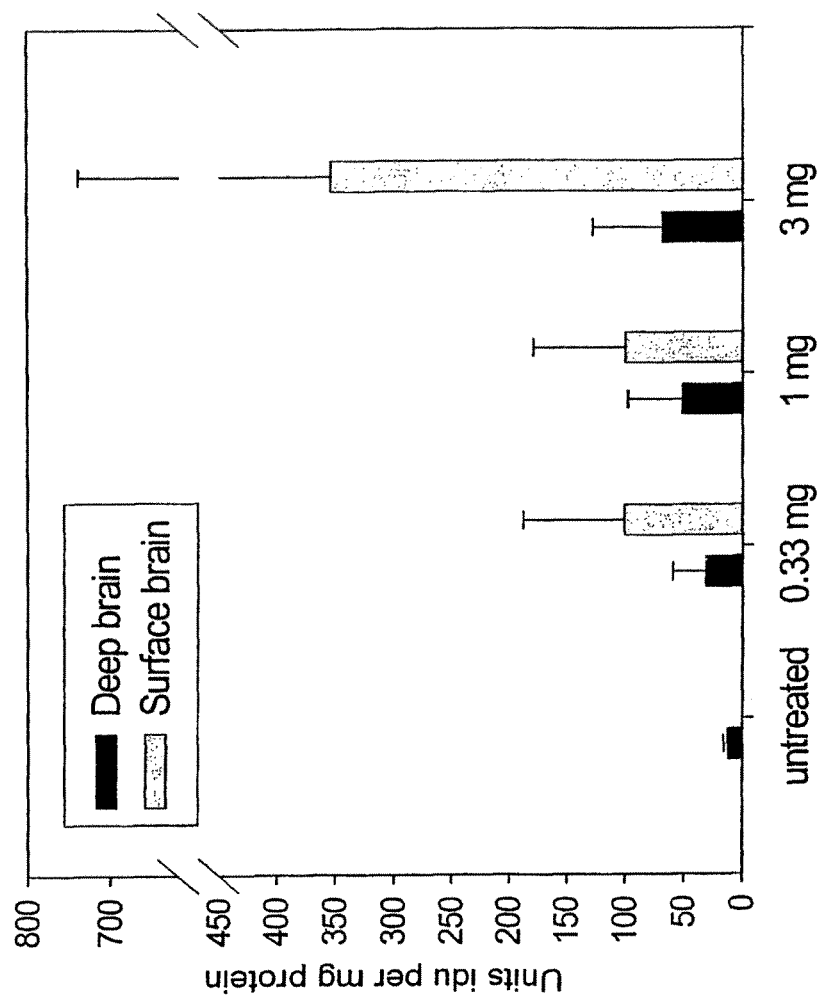
FIG. 2 describes levels of rh-iduronidase measured in deep brain and surface brain tissues in canines.
Figure 3:
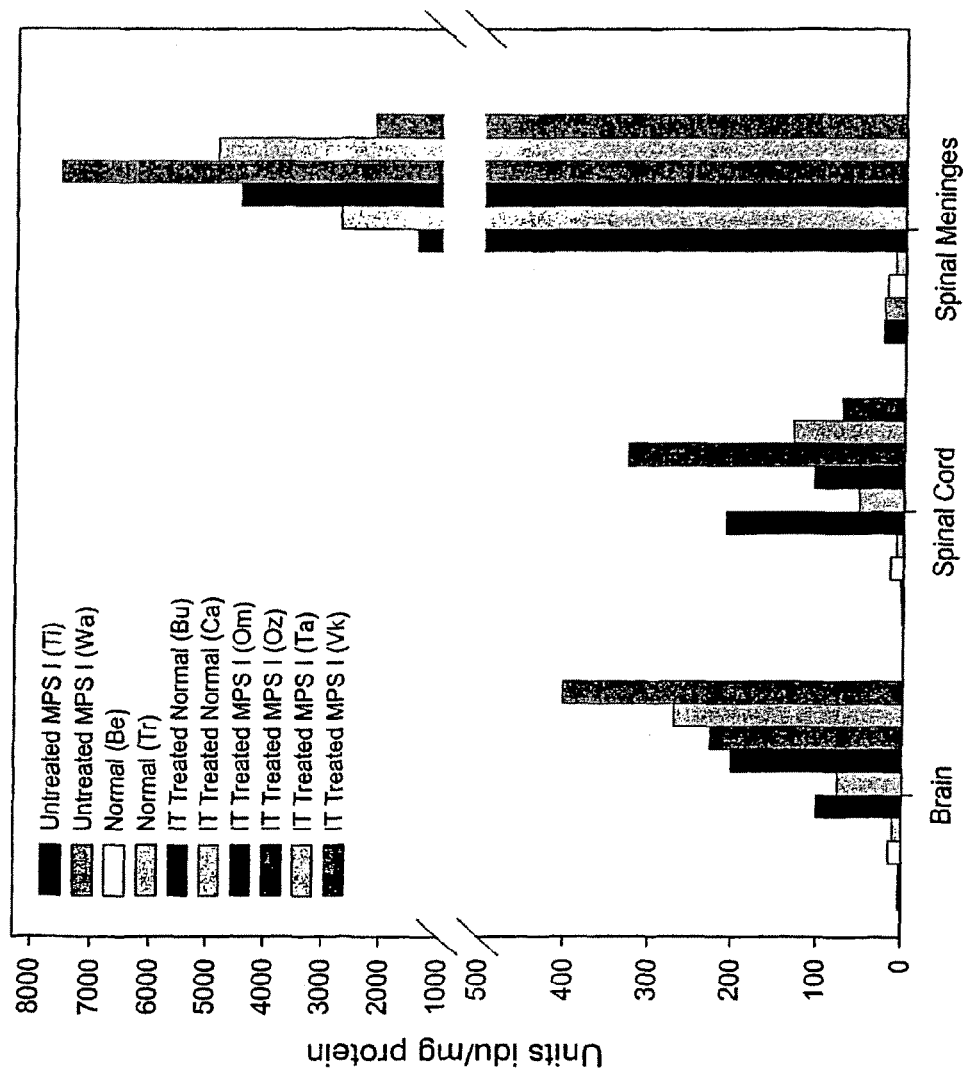
FIG. 3 describes levels of iduronidase activity in spinal cord and spinal meninges of iduronidase-treated MPS I animals.

Levels of rh-iduronidase were also measured in deep brain and surface brain tissues (FIG. 2) of animals given either 0.33 mg, 1 mg or 3 mg enzyme. Again, analyses showed that the higher the dose of enzyme the greater the amount of iduronidase detected in the brain tissue, with the 3 mg/injection group demonstrating a 5-fold increase in deep brain tissue. Iduronidase measured on the surface of brain tissue was detected at a 8-fold difference in animals receiving 0.33 mg protein/injection while animals receiving 3 mg/injection exhibited a 27-fold increase in surface expression of iduronidase compared to normal controls. Thus, while the majority of iduronidase is detected on the surface brain tissue, a significant amount penetrates into deep brain tissue, indicating this type of treatment would be a useful therapy for administration of enzymes in lysosomal storage disorders of deep brain tissue. Additional experiments in which the low, medium and high doses were 0.46 mg; 1.08/1.38 mg; and 4.14 mg, respectively, showed that deep brain specimens had 2.7, 4.4 and 5.9-fold of normal activity at these respective doses.

Immunohistochemical analysis by confocal microscopy showed that large amounts of rh-iduronidase could be detected on the surface of the cortex as well as inside cells of the hippocampus. Particularly, glial cells in the hippocampus, the part of the brain involved in memory, take up significant amounts of enzyme. Staining also demonstrated that the enzyme diffuses into the brain and some glial cells stain brightly with anti-iduronidase. The higher doses do not result in substantially higher α-L-iduronidase activity in the deep regions of the brain and hence, a dose of approximately 1 mg was selected for treating MPS I dogs in the further studies.

These results indicate that intrathecal injection of rh-iduronidase provides an efficient method for administering protein across the blood brain barrier. The protein is detectable both on the surface of brain cells and in lysosomes of brain cells, as shown in Example 2, demonstrating that intrathecal injection is an effective means for transporting enzymes involved in lysosomal storage disorders can be administered intrathecally and provide a therapeutic benefit to subjects affected by said disease.

EXAMPLE 4

Intrathecal Injection of Rh-Iduronidase Ameliorates MPS I Symptoms

Initial experiments demonstrated that iduronidase administered via intrathecal injection effectively crossed the blood brain barrier and could be detected in significant amounts in the lysosomes of neurons, on the surface of cerebral cortex cells, and also penetrated into deep brain tissue. Based on these results, it seems likely that lysosomal storage disorders that impair brain function could be treated via intrathecal injection of enzyme replacement therapy.

To assess the efficacy of intrathecal injection of enzymes involved in lysosomal storage disorders, canine subjects affected with the lysosomal storage disorder MPS I and lacking the enzyme iduronidase were treated with an intrathecal administration of rh-iduronidase. The iduronidase levels in the brain and central nervous system tissue assessed after 4 weeks of treatment.

As noted above, a dose of 1 mg rh-iduronidase/injection was selected. Four MPS I affected animals were treated with 1 mg rh-iduronidase/injection via intracisternal injection, one time per week for four weeks and enzyme levels measured 48 hours after the last treatment dose. The intrathecal injections resulted in widespread distribution of the enzyme in the brain, spinal cord, and meninges. Detection of enzyme activity in MPS I animals revealed a mean 21-fold increase in iduronidase levels in these animals compared to the control group. Analysis of enzyme activity in deep brain and surface brain tissue of MPS I animals showed an average of 11-fold and 37-fold increase in activity, respectively.

In a further set of experiments, the overall brain enzyme activity in the four treated dogs reached a mean 277 units/mg compared with a mean level of 11.9 units/mg in untreated normal dogs, and averaged 23-fold normal with a range of 17-34 fold normal levels. As was the case for the normal dogs, α-L-iduronidase activities were higher (3-4 fold) at the surface of the brain than its internal regions (474.0±257.7 vs. 138.7±93.5). Nevertheless, the levels in deep brain were still over 11 times normal.

Because intrathecal administration of a protein places the protein directly into the CSF, which bathes the entire central nervous system, it is likely that any protein injected via this route is detectable in all areas of the CNS. MPS I animals used above were used to assess the presence of iduronidase in the spinal cord and meninges of treated animals as described above in Example 1.

Spinal cord and meninges samples were obtained from four MPS I animals and iduronidase activity measured as above (mean of cervical, thoracic and lumbar regions). Spinal cord levels of iduronidase activity in MPS I animals was on average 13-fold higher than control animals while enzyme levels were approximately 300-fold higher in the spinal meninges of MPS I animals. In repeated experiments, the spinal the spinal cord, rh-iduronidase levels in intrathecally-treated MPS I dogs reached a mean of 160 units/mg or about 13 fold the normal level of 11.7 units/mg (p=0.022, Table 2). Penetration of enzyme was better in the cervical and thoracic regions than in the lumbar spine possibly due to incomplete distribution of enzyme from the cisterna magna injection site. RhIDU levels in treated MPS I dogs were 17-fold normal in the cervical spinal cord, 18-fold in the thoracic spine, and about 5-fold in the lumbar spine. In the spinal meninges, rh-iduronidase levels reached a mean 4,780 units/mg or over 300 fold greater than the normal levels of 15.4 units/mg (p=0.0018, Table 2). Even in the animal with the lowest level of enzyme penetration on average, iduronidase levels in the meninges reached 2,160 units/mg or 140-fold normal levels.

TABLE 2

Iduronidase levels in IT-treated MPS I dogs (~1 mg weekly dose)

| CNS Site | IT-treated [range] (n = 4) | Untreated/ Placebo-treated Normal (n = 5) | Ratio IT-treated vs. Normal |
|---|---|---|---|
| Brain | 277 ± 89.1 [203-403] | 11.9 ± 1.95 | 23.3 p = 0.0003* |
| Spinal cord | | | |
| Cervical | 196 ± 133 [43.3-367.3] | 11.1 ± 1.69 | 17.7 |
| Thoracic | 224 ± 138 [132.4-428.7] | 12.0 ± 3.10 | 18.7 |
| Lumbar | 59.8 ± 85.9 [8.8-188.0] | 12.1 ± 2.90 | 4.9 |
| Average | 160 ± 115 [73.1-328.0] | 11.7 ± 0.57 | 13.7 p = 0.0216* |
| Spinal Meninges | | | |
| Cervical | 7030 ± 3480 [4060-11,100] | 15.6 ± 4.85 | 451 |
| Thoracic | 5490 ± 4200 [1570-9970] | 14.6 ± 3.34 | 376 |
| Lumbar | 1810 ± 2690 [95.4-5820] | 16.1 ± 9.10 | 112 |
| Average | 4780 ± 2220.0 [2160-7580] | 15.4 ± 0.76 | 308 p = 0.0018* |

Iduronidase levels are calculated from mean values for each region for each dog sacrificed. Iduronidase levels are expressed in units of iduronidase per mg protein. Means of the means for each animal ± standard deviation are shown. Ranges for each data set are mean values of iduronidase assays in each tissue type for each dog.
*Statistically significant.

EXAMPLE 5

Intrathecal Treatment of Iduronidase Reduces GAG Levels in MPS I Animals

A significant factor in the debilitation of subjects with lysosomal storage disorders such as MPS I is the lack of breakdown of macromolecules resulting in a build up of glycosaminoglycans in the lysosomes of cells. It is hypothesized that enzyme replacement therapy via intrathecal injection should enhance the breakdown of GAGs and return GAG levels to those comparable to normal individuals.

To test the ability of recombinant iduronidase treatment to ameliorate GAG storage in MPS I subjects, MPS I canines treated as above were assayed for brain lysosomal levels of glycosaminoglycans. Brain levels in MPS I animals receiving rh-iduronidase were reduced to normal or below normal levels whereas untreated MPS I animals demonstrated GAG levels approximately 2× that of normal subjects. GAG levels measured in spinal meninges were 7 times normal levels in untreated MPS I animals, but decreased by 57% to 3 times normal levels in MPSI animals receiving intrathecal iduronidase.

Figure 4:
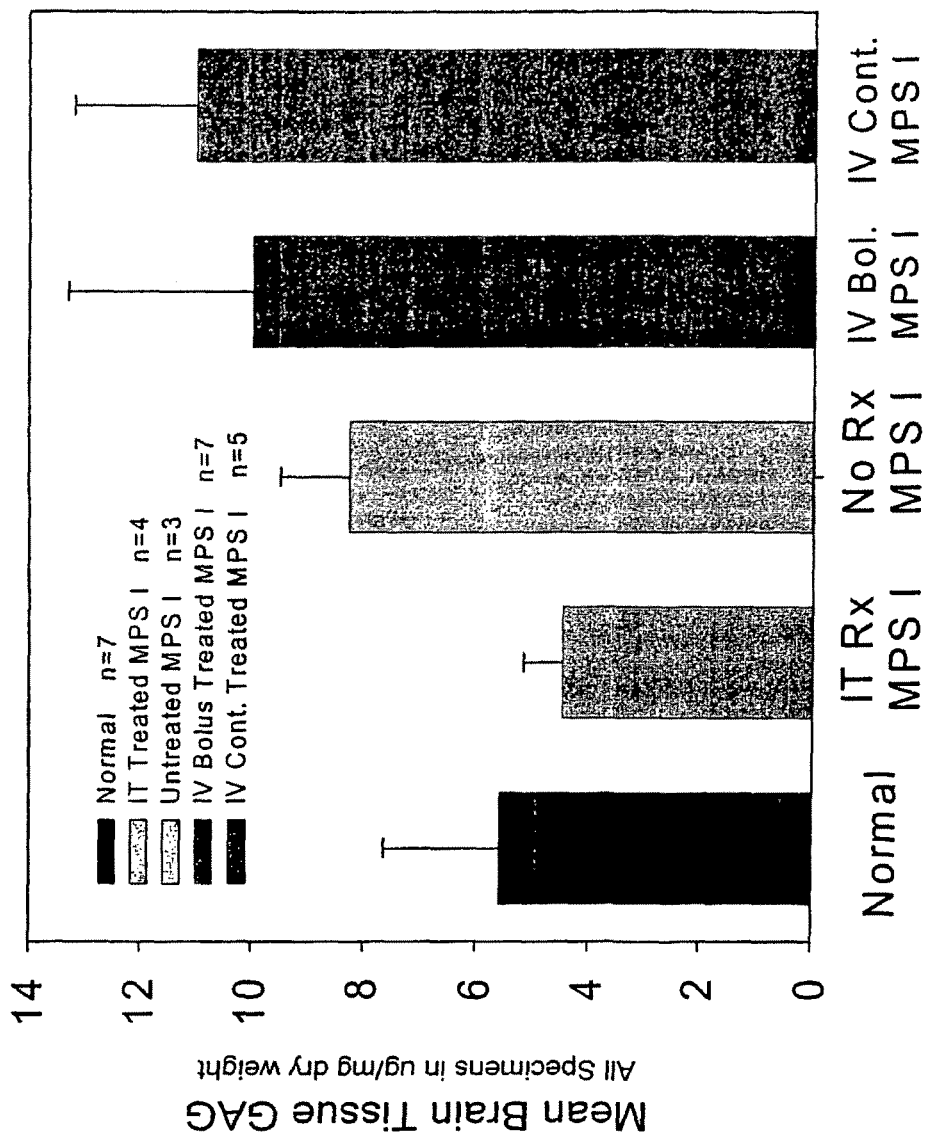
FIG. 4 describes a comparison of glycosaminoglycan (GAG) levels in MPS I treated animals receiving either intrathecal or IV administration of iduronidase.

GAG levels were also compared in MPS I treated animals receiving intrathecal or IV (either a single bolus, weekly bolus, monthly bolus, quarterly bolus, bolus administered every six months, annual bolus or alternatively, administered continuously) treatment with rh-iduronidase (FIG. 4). GAG levels in MPSI animals receiving IV iduronidase treatment were similar to, or slightly higher, than levels observed in untreated MPS I animals (approximately 10 µg/mg compared to approximately 8 µg/mg, respectively). Intrathecal administration of iduronidase reduced brain GAG levels to below normal, exhibiting approximately 4 µg/mg protein, or 2-fold less than untreated MPS I animals.

In further experiments, it was again demonstrated that the many-fold increase in normal levels of rh-iduronidase activity in the brains of treated MPS I dogs led to significant decreases in GAG levels relative to the untreated control MPS I dogs and reached normal GAG levels (Table 3). The mean levels of GAG in the brains of MPS I dogs treated with intrathecally with rh-iduronidase were 4.47±0.69 µg/mg dry weight compared with 8.26±1.23 µg/mg for the untreated MPS I dogs (p=0.0017).

The GAG level in the brains of the intrathecally-treated dogs was not significantly different from that of untreated normal dogs (5.43±1.95, n=8, p=0.37). The brain GAG levels in intrathecally-treated MPS I dogs was also considerably below that of MPS I dogs treated in prior studies with IV infusions of rhIDU (10.4±2.14, n=12, Table 3). Since increasing age can result in increased storage, the brain GAG content was also plotted against canine age for control, IV-treated and IT-treated dogs. The plot further corroborates the normalization of total GAG for IT-treated dogs when comparing control or IV-treated dogs of comparable age.

Meningeal GAG levels were analyzed in samples derived from the cervical, thoracic and lumbar regions (Table 3). Overall, the mean spinal meninges GAG level of IT-treated dogs decreased 57%, to 15.3 µg/mg (range 9.33 to 22.5 µg/mg) compared with an untreated canine mean of 35.9 µg/mg. This represents a decrease from a level 7-fold normal in untreated MPS I dogs to 3-fold normal in the treated animals and was statistically significant (p=0.009). Samples from the cervical and thoracic meninges often had better GAG clearance than the more distal lumbar meninges. Mean total GAG levels in the spinal cords of the IT-treated MPS I dogs decreased to 3.43 µg/mg compared with 5.04 µg/mg for untreated MPS I dogs, but the total levels were relatively low, and the change was not statistically significant.

TABLE 4

Glycosaminoglycan levels in untreated MPS I, IT-treated MPS I, IV-treated MPS I, and untreated normal dogs

| CNS Site | MPS I untreated [range] | MPS I IT-treated [range] | Ratio IT-treated to untreated MPS I | MPS I IV-treated [range] | Ratio IT-treated to IV-treated MPS I | Normal untreated [range] | Ratio IT-treated MPS I to normal |
|---|---|---|---|---|---|---|---|
| Brain | 8.26 ± 1.23 [6.91-9.56] n = 4 | 4.47 ± 0.69 [3.63-5.26] n = 4 | 0.54 p = 0.0017* | 10.4 ± 2.14 [7.42-16.6] n = 12 | 0.43 p = 0.0001* | 5.43 ± 1.95 [2.95-8.31] n = 8 | 0.82 p = 0.37 |
| Spinal Cord | | | | | | | |
| Cervical | 3.52 ± 0.56 [3.12, 3.91] | 2.99 ± 0.50 [2.71-3.73] | | — | | 1.84 ± 0.84 [0.93-2.59] | |
| Thoracic | 5.50 ± 0.77 [4.95, 6.04] | 2.56 ± 0.77 [1.90-3.68] | | — | | 2.11 ± 1.03 [1.29-3.26] | |
| Lumbar | 6.11 ± 1.47 [5.07, 7.15] | 4.75 ± 1.08 [3.53-5.73] | | — | | 5.49 ± 0.63 [4.81-6.06] | |
| Average | 5.04 ± 0.93 [4.38, 5.70] n = 2 | 3.43 ± 0.72 [2.72-4.38] n = 4 | 0.68 p = 0.075 | — | | 3.14 ± 0.81 [2.34-3.97] n = 3 | 1.09 p = 0.64 |
| Spinal Meninges | | | | | | | |
| Cervical | 20.0 ± 1.98 [18.6, 21.4] | 10.8 ± 2.45 [9.07-14.4] | | — | | 4.51 ± 0.51 [3.92-4.86] | |
| Thoracic | 40.5 ± 0.95 [39.8, 41.2] | 13.4 ± 4.30 [7.05-16.4] | | — | | 4.35 ± 1.47 [3.05-5.94] | |
| Lumbar | 47.2 ± 12.0 [38.6, 55.7] | 21.6 ± 13.8 [10.6-41.7] | | — | | 5.17 ± 2.53 [2.33-7.21] | |
| Average | 35.9 ± 3.03 [33.8, 38.0] n = 2 | 15.3 ± 5.56 [9.3-22.5] n = 4 | 0.43 p = 0.009* | — | | 4.68 ± 0.97 [3.75-5.69] n = 3 | 3.26 p = 0.024* |

GAG levels are calculated from mean values for each region for each dog sacrificed and are expressed in µg/mg dry weight. Means of the means for each animal ± standard deviation are shown.
IV treatment weekly dose ranged from 0.5 to 2.0 mg/kg for 3-15 months.
*Statistically significant These results show that intrathecal treatment of MPS I is an efficient means for reducing the debilitating storage in these lysosomal storage disorders, such as macromolecule build-up in tissue lysosomes, and is more effective at reducing GAG levels that standard IV administration of iduronidase enzyme replacement therapy.

EXAMPLE 6

Reduction of Lysosomal Pathology after Intrathecal rhIDU

In canine MPS I, the most prominent lysosomal storage on brain histology is present in the perivascular mesenchymal cells that lie close to the brain capillaries, separated from the bloodstream by the blood-brain barrier. To determine the extent of the storage disease in MPS I affected animals, pathological analysis was performed by electron microscopy to detect GAG deposits in brain tissue. MPS I animals were treated with 1 mg iduronidase in weekly doses (4×) as described above in Example 1.

Figure 5:
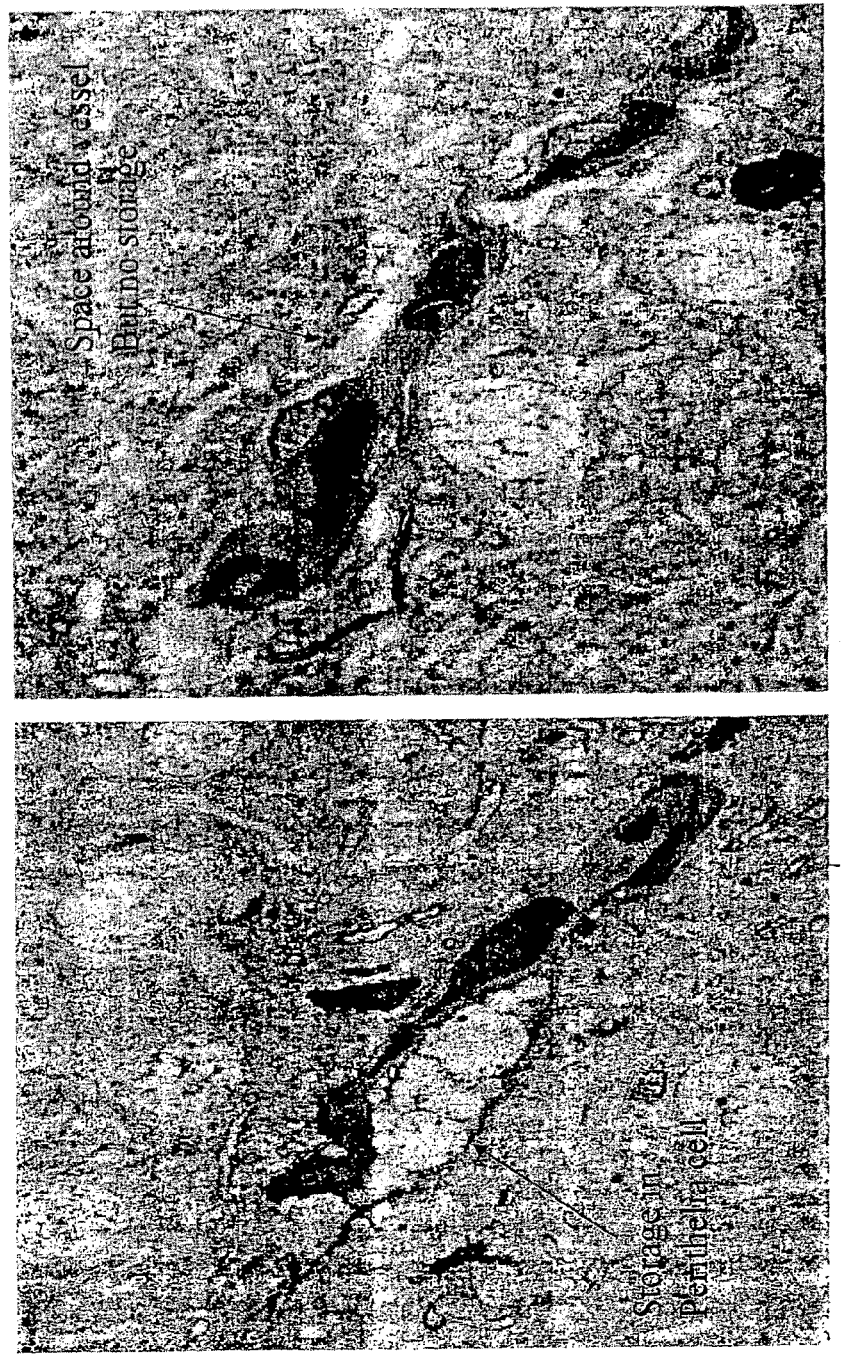
FIG. 5 depicts electron microscopy (in brain sections) of GAG storage in perivascular macrophage disease of iduronidase treated and untreated MPS I animals.
Figure 6:
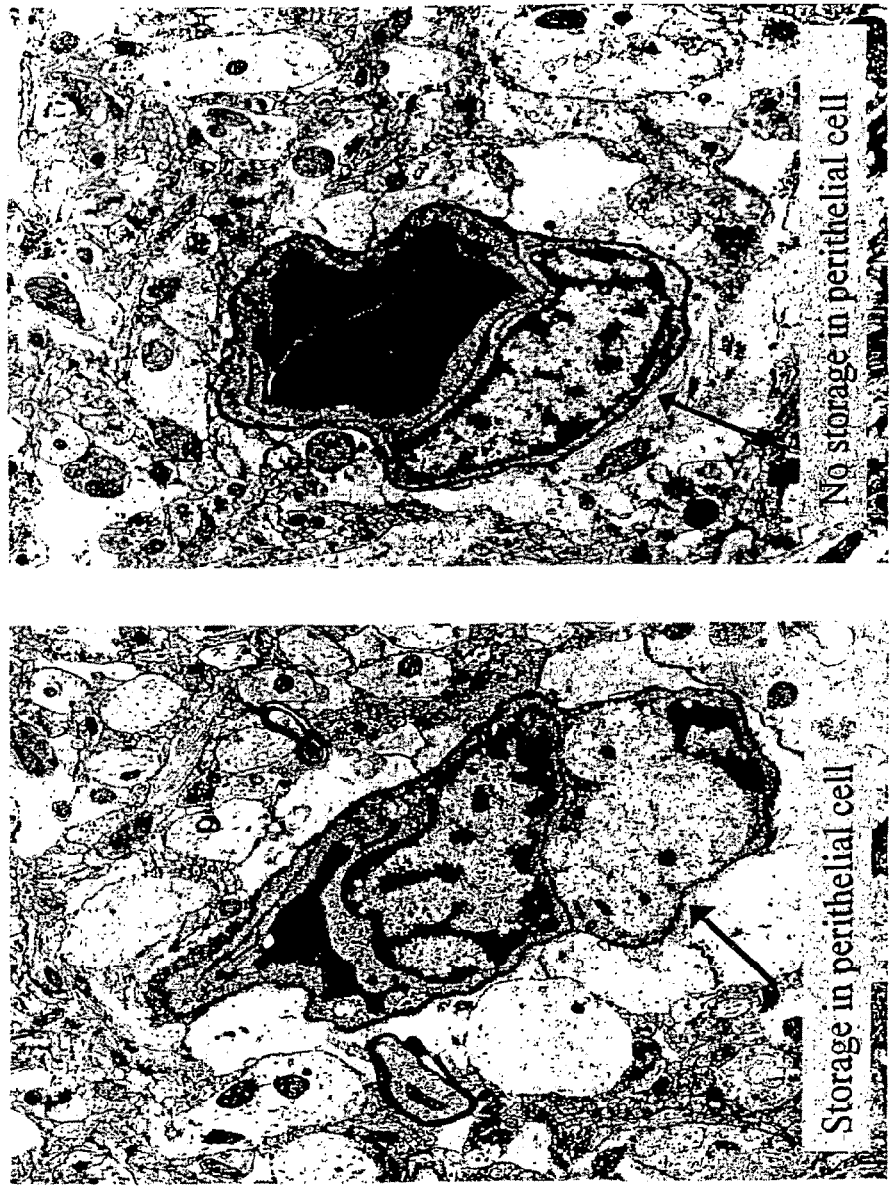
FIG. 6 is a greater magnification of electron microscopy (brain sections) of GAG storage in perivascular macrophage disease of iduronidase treated and untreated MPS I animals, which demonstrates that perivascular cells in treated MPS I animals lack GAG storage.
Figure 7:
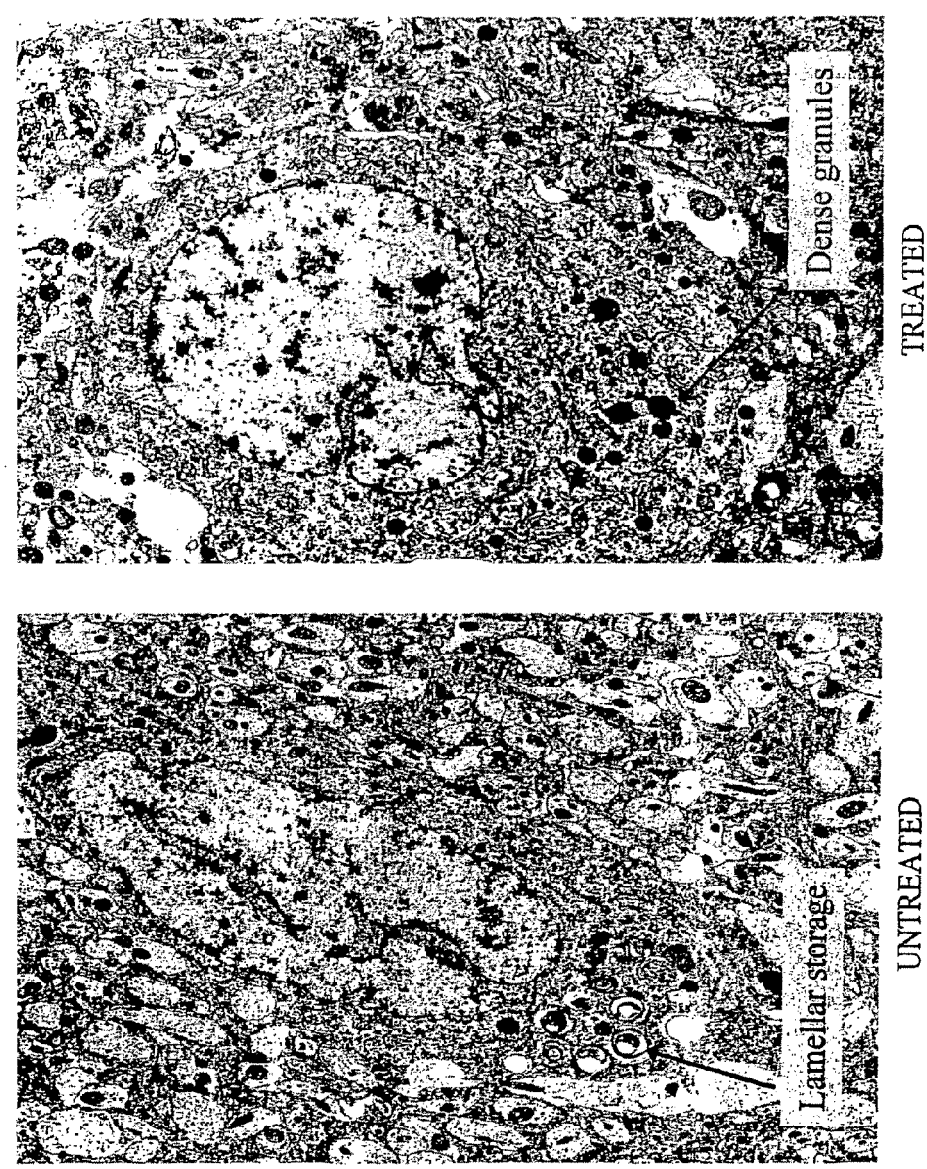
FIG. 7 is a comparison of neuron disease pathology in iduronidase treated and untreated MPS I animals which shows that treated animals are free of lamellar GAG storage.
Figure 8:
FIG. 8 is a comparison of brain sections assessed for meningeal disease in treated or untreated MPS I animals which shows the absence of large GAG-filled foam cells in the meninges of treated animals, as compared to controls.
Figure 9:
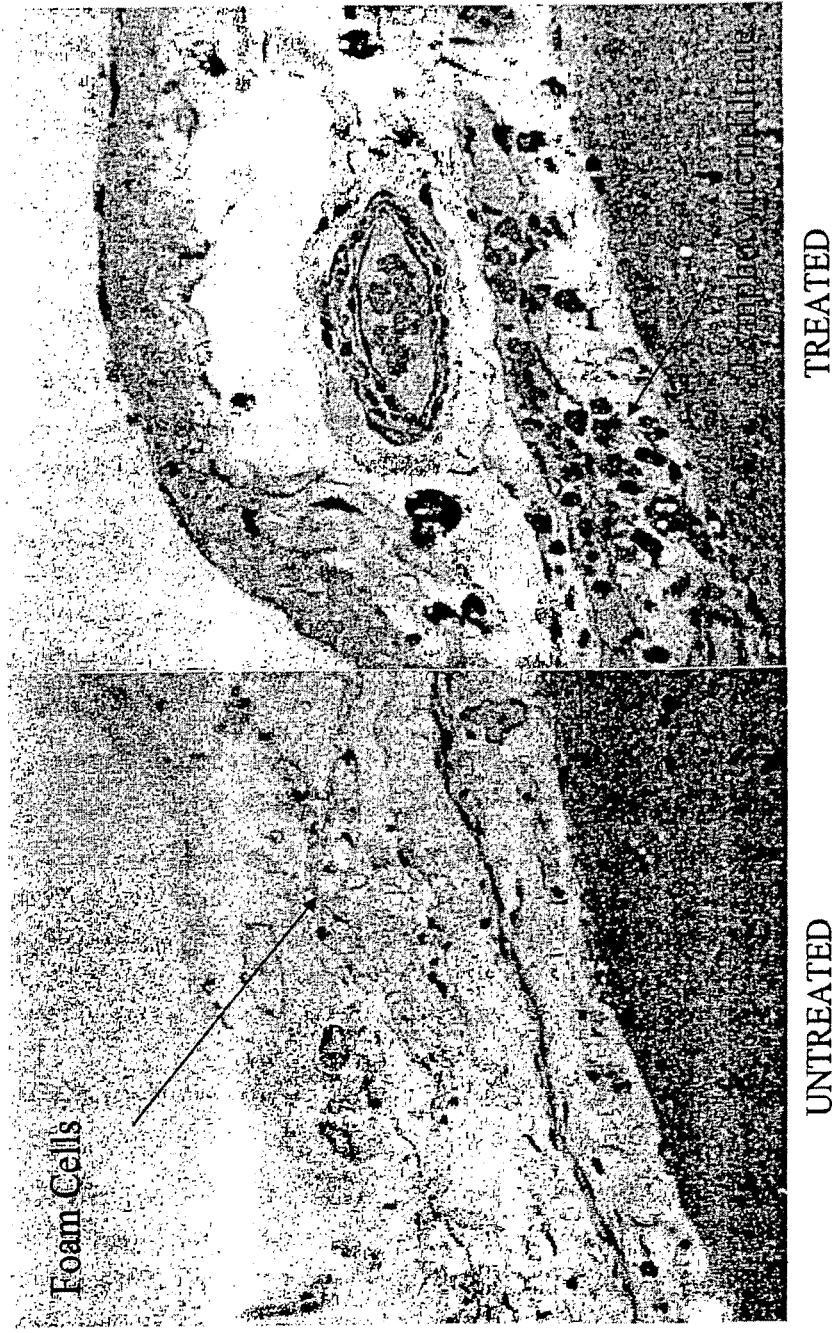
FIG. 9 illustrates that brain sections of MPS I treated animals exhibit minor lymphocytic infiltrate into the meninges.

Tissue taken from untreated MPS I animals with perivascular macrophage disease demonstrate distinct GAG storage in perithelial cells whereas treated animals exhibit a space around storage vessels, with no GAG storage (FIG. 5 and FIG. 6). Analysis of neuron disease pathology in MPS I animals reveals that untreated animals show lamellar storage of GAG and gangliosides while iduronidase treated animals exhibit dense granules with minimal storage of the macromolecule (FIG. 7). On electron micrographs, ultrastructurally the total amount of storage in neurons in untreated MPS I dogs was modest. The membrane-bound, granular, flocculent, membranous, cytoplasmic and zebra body neuronal storage was decreased in the treated MPS I dogs. However, aggregates of electron-dense, complex, lipofuscin-like material did remain in the treated MPS I animals. Brain sections assessed for meningeal disease in treated or untreated MPS I animals demonstrated the presence of large foam cells in the meninges of untreated animals while meninges of iduronidase treated animals were free of engorged foam cells containing GAG (FIG. 8). Brain sections of MPS I treated animals did exhibit minor lymphocytic infiltrate into the meninges (FIG. 9). Thus, intrathecally-treated MPS dogs showed a dramatic reduction in perivascular cell storage in both surface and deeper areas of the brain (see FIGS. 5 and 6). GAG storage was also reduced in the glia of the brains of intrathecally-treated MPS I dogs. Focal reduction in neocortical GAG storage was also seen in three of the four IT-treated MPS I dogs. GAG storage was also reduced in the spinal meninges of treated animals on toluidine blue stained thick sections. Spinal meningeal foam cells were less frequently observed in the four MPS I dogs treated with rhIDU than in the untreated MPS I dogs, and there was some patchiness to the pattern of clearance.

Overall indications are that intrathecal administration of iduronidase facilitates clearance of glycosaminoglycans for the brain and meninges of treated subjects, reducing levels back to those observed in normal subjects. It was also observed that intrathecal delivery of enzyme causes lymphocytic infiltrate into the meninges, perhaps generating an immune response that is effective in clearing inappropriate storage of materials. Analysis of clinical symptoms of lysosomal storage disorders showed that intrathecal iduronidase treatment of MPS I animals reduced cord compression-induced weakness and resolved nystagmus in these animals.

The effectiveness of intrathecal iduronidase treatment over standard IV techniques indicates that this method of enzyme replacement therapy is effective for relieving the symptoms of MPS I subjects and is readily applicable to other common lysosomal storage disorders described above.

EXAMPLE 7

Immune Response and Other Adverse Effects

Moderate levels of antibody against rh-iduronidase were detected in both the serum (up to 202 units/$\mu$L) and CSF (up to 82.0 units/$\mu$L) of two MPS I dogs and one normal dog treated with rhIDU (Table 4). All three of these animals had prior exposure to intravenous rhIDU months before entry into the study. For the remaining treated animals, low levels of antibodies to rhIDU were detected in the serum (3.61 to 40.9 units/$\mu$L at study end), and lower levels were detected in the CSF (1.39 to 2.28 units/$\mu$L). There were modest increases in CSF leukocyte counts in the treated dogs. In all dogs (normal and MPS I) treated with IT rhIDU, there were variable accumulations of B-lymphocytes, plasma cells and other lymphocytes in the meninges of the spinal cord, areas of the spinal dura and around the brain. These dural infiltrates were typically most intense around spinal nerve roots and in more severely affected cases extended into the adjacent extradural fat and connective tissue. In one such case there was also a moderate focal extradural lymphocytic arteritis. There was no meningitis or inflammation in untreated animals, with the exception of one normal dog who received vehicle. Two normal dogs treated with rhIDU developed a mild meningitis. The extent of the CNS inflammatory response varied among dogs and appeared to be dose-related. There were no clinically apparent effects of the immune response observed; the dogs appeared well and active.

TABLE 5

ELISA titer of antibodies to rhIDU in CSF of IT-treated dogs

| Canine | Week 1 | Week 2 | Week 3 | Week 4 | End of treatment |
|---|---|---|---|---|---|
| IT-treated MPS I dogs | | | | | |
| Om | 0.001 | 0.000 | 0.166 | 2.09 | 2.28 |
| Oz | 0.007 | 0.000 | 0.046 | 1.08 | 1.57 |
| Ta† | 0.000 | 0.473 | ND | 45.0 | 52.0 |
| Vk† | 0.000 | 4.16 | 53.1 | 81.5 | 82.0 |
| IT-treated normal dogs | | | | | |
| Xu | 0.011 | 0.008 | 0.014 | 1.35 | ND |
| Xi | 0.012 | 0.015 | 0.024 | 2.49 | ND |
| Bu | 0.030 | 0.009 | 0.670 | 1.43 | 1.39 |
| Ca† | 0.105 | 3.08 | 31.1 | 30.7 | 32.8 |
| Dv | 0.007 | 0.000 | 0.526 | 1.57 | 1.90 |
| Df | 0.004 | 0.000 | 0.025 | 0.670 | 2.25 |

Titers expressed in OD units per $\mu$L undiluted CSF. ND = not done.
*Om, Oz and Bu received 1.08 mg, Ta, Vk, and Ca received 1.38 mg, Xu and Xi received 4.14 mg, and Dv and Df received 0.46 mg of IT rhIDU.
†Ta, Vk, and Ca had exposure to rhIDU months prior to study entry The administration of any protein product carries a risk of an immune response, either in the form of chronic antibody formation or an inflammatory response. As seen above, immune responses were observed in canines treated with intrathecal rh-iduronidase. Antibodies to $\alpha$-L-iduronidase were found in the serum and CSF of three dogs who had had exposure to intravenous enzyme prior to entry into this study. Other than the lymphoplasmacytic infiltrate, there were no obvious clinical adverse effects of this immune response.

The intrathecal-based treatments of MPS and other disorders as described herein may advantageously be administered in combination with a regimen that produces immune tolerance to the agent being delivered. Particularly contemplated immune tolerance methods include those described in e.g., U.S. Patent Publication No. 20030211113 and U.S. Patent Publication No. 20040009906, each incorporated herein by reference in its entirety. Further examples of immune tolerance protocols are provided in Example 9.

EXAMPLE 8

Treatment of MPS I Subjects With Recombinant Iduronidase

The successful treatment of MPS I canines with recombinant human iduronidase indicates that intrathecal enzyme replacement therapy provides effective treatment of human subjects with MPS I.

To treat human MPS I patients with rh-iduronidase, patients with mucopolysaccharidosis I are selected for treatment. The subjects are evaluated at base line and at 6, 10, 14, 18, 22, 26, and at least once monthly up to 52 weeks by detailed clinical examinations, magnetic resonance imaging of the abdomen and brain, echocardiography, range-of-motion measurements, polysomnography, clinical laboratory evaluations, measurements of leukocyte α-L-iduronidase activity, and urinary glycosaminoglycan excretion. The subjects should also be assessed for the CNS symptoms that result from lysosomal storage granules in the brain. Such symptoms include developmental delay and/or regression in development of the subject suffering from the disease, which can be clinically assessed, for example, using Bayley's Scales of Infant Development II (including monitoring a motor and developmental quotient), monitoring language or other intellectual and motor developments, monitoring evoked potential tests such as auditory or other evoked potential testing. Another symptom, high pressure hydrocephalus caused by the presence of storage granules in the cerebral meninges near the arachnoid granulations, may be clinically monitored and assessed using art-recognized methods for determining CSF pressure via lumbar puncture and/or via an intraventricular catheter. Lysosomal storage in the cervical meninges near the cord at C1-C5 or elsewhere along the cord also may be clinically assessed, which manifests as progressive compressive spinal cord compression with lower extremity weakness, loss of bowel and bladder control and sensory deficits also could be monitored. Such symptoms may be monitored using e.g., neurological examination for abnormal Babinski's reflexes, deep tendon reflexes, motor function or sensation. Neurophysiological deficits of spinal cord compression may be assessed using somatosensory evoked potentials. Magnetic resonance imaging with or without a contrast agent may also be used to identify the anatomic location of compression as well as an evaluation of edema or other indicia of cord injury at the site of compression. Perivascular storage of lysosomal storage granules can be assessed by determining the presence of cysts around the vessels, which may also be assessed using MRI scans to determine the size and number of such cysts. Monitoring these symptoms before and after the treatment will allow an assessment of the efficacy of the therapeutic intervention.

Iduronidase is administered to subjects via intrathecal infusion (diluted in normal saline with 0.1 percent human serum albumin) at a dose of for example, 1 mg iduronidase per 20 kg of animal weight, delivered weekly. Intrathecal administration is performed via direct injection into the CSF or as in Penn et al., (*Neurosurgery.* 40:94-9. 1997), via a drug pump implanted into the lumbar subarachnoid space, e.g. a Medtronic SYNCHROMED® pump or similar device, for intrathecal delivery. The pump is implanted according to manufacturer's directions and may be implanted at any level appropriate for the subject or disorder being treated. For example, the tip of the pump's catheter may be placed at the T-10 level in the spine. Subjects are premedicated with diphenhydramine (0.5 to 1.25 mg per kilogram of body weight).

In initial therapy, iduronidase is given to affected subjects weekly for a four week period. Administration may be continued for extended periods of time depending on the severity of MPS I disease in the subject being treated as well as the age, weight, or sex of the subject. Dosage amounts and duration may be determined by the attending physician.

Subjects are assessed for change in symptoms of MPS I using motor skills tests, MRI analysis of GAG tissue deposits, and GAG levels in urine at the timepoints noted above. For instance, urinary GAG levels in MPS-I subjects are compared to normal excretion values. There is a wide range of urine GAG values in untreated MPS-I subjects. A greater than 50% reduction in excretion of undegraded GAGs following therapy with the rh-iduronidase is a valid means to measure an individual's response to therapy. For example, data is collected measuring the leukocyte iduronidase activity and buccal iduronidase activity before and after therapy in MPS I subjects.

Increased motor ability or decreased evidence of GAG deposits in the brain or GAG levels in urine are indicative that rh-iduronidase treatment is successfully breaking down excess GAG in the treated subjects and relieving symptoms of the disease.

EXAMPLE 9

Antigen-Specific Tolerance and Intrathecal Enzyme Replacement Therapy in the Treatment of Lysosomal Storage Disorders As noted above, intrathecal iduronidase treatment of MPS I affected animals resulted in lymphocytic infiltrate into the meninges of treated animals. This may be due to an overreaction by the immune system to the presence of large amounts of foreign antigen delivered to the animal. To overcome these types of reactions, methods of antigen-specific tolerance have been used to successfully suppress the immune system. Co-owned, co-pending U.S. Patent Application No. describes a regimen of treating MPS I canines which entails induction of antigen-specific tolerance and intravenous administration of iduronidase replacement therapy. Based on the results described herein, which indicate that intrathecal enzyme administration is more effective than intravenous injection at decreasing GAG storage in the brain and relieving clinical symptoms of MPS I, it follows that use of intrathecal injection coupled with antigen specific tolerance will provide greater relief to subjects suffering from MPS I.

Subjects with mucopolysaccharidosis I are selected for treatment. The subjects are evaluated at base line and at 6, 12, 26, and 52 weeks by detailed clinical examinations, magnetic resonance imaging of the abdomen and brain, echocardiography, range-of-motion measurements, polysomnography, clinical laboratory evaluations, measurements of leukocyte α-L-iduronidase activity, and urinary glycosaminoglycan excretion.

Cyclosporin A (Neoral or Sandimmune) and Azathioprine (Imuran) are obtained from commercial sources. Both drugs are dosed orally at the dose and frequency as follows: CsA Neoral® 12.5 mg/kg/every day divided bid po; Aza Imuran®

5 mg/kg qod po for two weeks conditioning period. The drugs are then administered at that dose for an additional two weeks in the presence of toleragen. Doses are halved for all drugs each 2 weeks after first toleragen infusion. Subjects are monitored for adverse reactions, and for CsA peak and trough levels. The CsA is preferably at a level greater than 400 ng/ml.

Recombinant α-L-iduronidase is produced in Chinese-hamster-ovary cells with the use of bioreactors and standard column chromatography, and extensively analyzed for safety and purity. The activity of α-L-iduronidase is measured according to the method of Shull et al. supra., or with an assay whose results are reported in SI units (Kakkis et al., *Mol Genet Metab.* 2001, 72(3):199-208; Kakkis et al., *N Engl J. Med.* 2001; 344(3):182-8). When the latter assay is used, a dose of 125,000 U of α-L-iduronidase per kilogram is equivalent to 100 SI units per kilogram. Urinary glycosaminoglycan excretion is measured according to an adaptation of the method of Bjontsson. Enzyme-linked immunosorbent assays for antibodies to α-L-iduronidase uses a variation of the method of Shull et al., and Western blotting is performed according to a standard method.

The toleragen is administered by intravenous infusion (diluted in normal saline with 0.1 percent human serum albumin) at a dose of 0.056 mg/kg, delivered weekly. After tolerization to iduronidase, intrathecal treatment with the enzyme composition is affected as described herein. In a preferred embodiment, the methods of the present example were tested on dogs treated monthly using a 1 mg injection of rh iduronidase as a toleragen. After 4 injections over a three month period, the GAG levels in the brains of these animals were observed as normal. The administration protocol is preferably effective such that the 1 mg injections are administered quarterly or every 6 months.

Intrathecal administration for use in the present methods is performed via direct injection into the CSF or as in Penn et al., (*Neurosurgery.* 40:94-9. 1997), via a drug pump implanted into the lumbar subarachnoid space, e.g. a Medtronic SYNCHROMED® pump or similar device, for intrathecal delivery. The pump is implanted according to manufacturer's directions and may be implanted at any level appropriate for the subject or disorder being treated. For example, the tip of the pump's catheter may be placed at the T-10 level in the spine. The first dose is given after completion of the two week conditioning period, and weekly thereafter. Subjects are premedicated with diphenhydramine (0.5 to 1.25 mg per kilogram of body weight).

After induction of tolerance, preferably 12 wee after initiation of the conditioning period, the dose is increased to once weekly, 0.58 mg per kilogam.

Subjects are assessed for change in one or more indicators of the symptoms of brain disease associated with lysosomal storage disease after treatment with recombinant iduronidase. Such indicators include but are not limited to changes in development, motor function, maintenance of development over time, decreased CSF pressure, decreased neurological symptoms by complaint or by examination, decreased cord compression as examined by MRI analyses of the neck or spine and somatosensory evoked potentials after treatment with recombinant iduronidase. It is predicted that iduronidase treatment increases the breakdown of excess GAG in the brain and spinal cord of affected individuals and releases the pressure exerted on the spinal cord. An improvement in motor ability is indicative of a decrease in cord compression as a result of iduronidase treatment.

EXAMPLE 10

Intrathecal Treatment of Other Lysosomal Storage Diseases

The above methods are useful in the treatment of human subjects manifesting a clinical phenotype of deficiency of any lysosomal enzyme. All subjects manifest some clinical evidence of visceral and soft tissue accumulation of glycosaminoglycans or other macromolecule with varying degrees of functional impairment. The diseases that are treated or prevented using the methods of the present invention are: Mucopolysaccharidosis II (MPS II), MPS IIIA, MPS IIIB, Metachromatic Leukodystrophy (MLD), Krabbe, Pompe, Ceroid Lipofuscinosis, Tay-Sachs, Niemann-Pick A and B, Gaucher Disease, and other lysosomal diseases as described above.

For each disease the enzyme administered in the intrathecal enzyme replacement therapy or during the tolerization regimen would comprise a specific compound or enzyme. For methods involving MPS H, the preferred compound or enzyme iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

The enzyme may be administered at doses appropriate for the subjects begin treated and are generally delivered based on a mg/kg ratio as described in the Detailed Description. Subjects receiving enzyme are monitored for enzyme levels in blood and tissue samples and for other symptoms particular to the lysosomal storage disorder being treated. For instance, subjects with Gaucher. Disease (Type 3) who exhibit diminished motor skills or myclonic seizures due to aberrant lipid storage are monitored for improvement in motor skills and decrease in seizure frequency after intrathecal administration of glucoerebrosidase replacement therapy.

Improvement in one or more symptoms of a lysosomal storage disorder after intrathecal administration of an enzyme deficient in the lysosomal storage disorder demonstrates that this route of administration is a new and useful method for the treatment of lysosomal disorders affecting human subjects.

EXAMPLE 11

Monthly Intrathecal Treatment Regimen

As discussed herein throughout intrathecal administration of rhIDU has been shown to effectively penetrate the CNS. In certain exemplary studies, weekly doses of approximately 1 mg of rhIDU given intrathecally have been shown to penetrate the CNS and reduce glycosaminoglycan (GAG) storage in canine mucopolysaccharidosis I (MPS I). Further studies described in the present example show that monthly, rather than weekly treatments, also are effective.

Figure 10A:
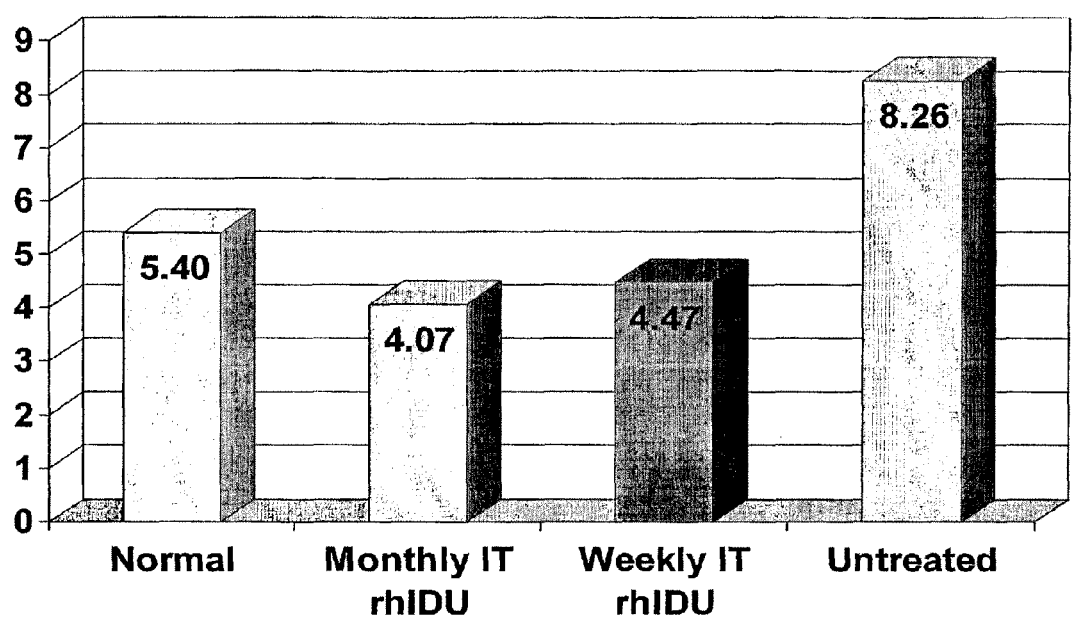
FIG. 10A through 10C provide comparisons of the effects of monthly vs. weekly intrathecal administration of rhIDU.
Figure 10B:
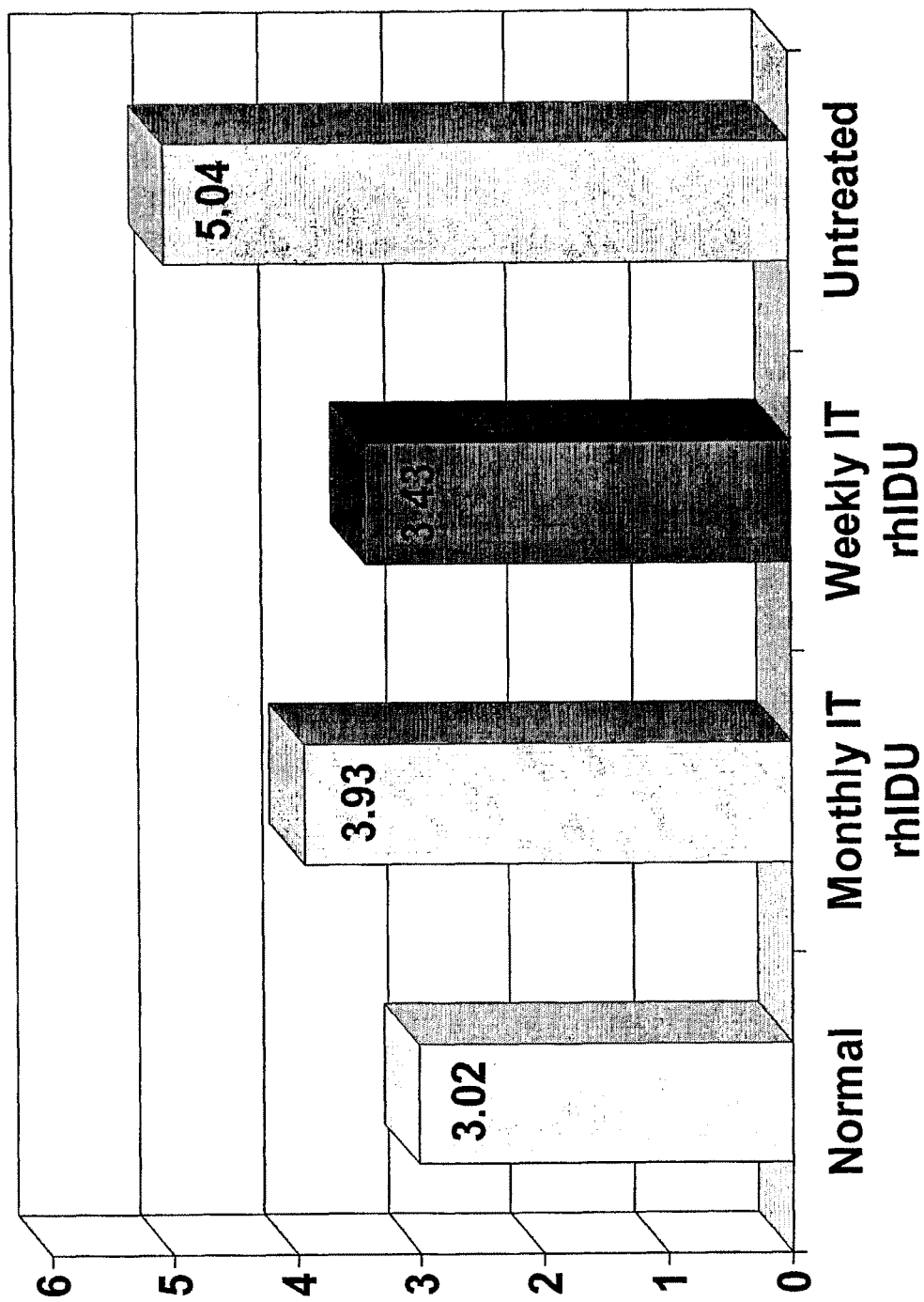
Figure 10C:
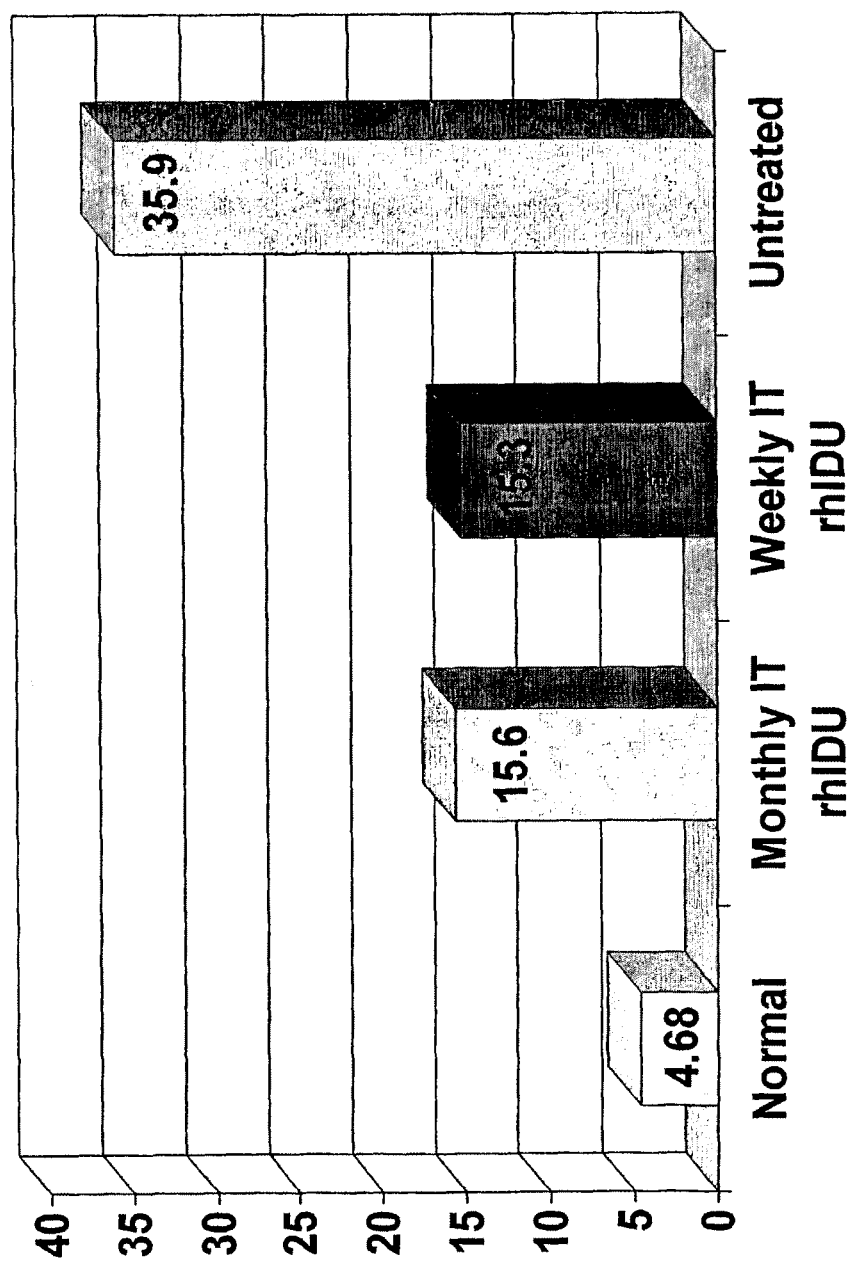

Three MPS I dogs received 4 monthly doses of ~1 mg IT rhIDU in combination with weekly IV rhIDU. In this combined regimen, it was seen that iduronidase levels reached 23-fold normal levels in the brain, 7-fold in the spinal cord, and 423-fold levels in the meninges of dogs treated monthly, vs. 23-fold, 13-fold, and 300-fold in 4 dogs treated weekly with intrathecal rhIDU only. Brain GAG reached normal levels in both regimens. With monthly treatment, a 51% reduction in brain GAG storage (vs. 46% with weekly IT administration; FIG. 10A) was observed, a 22% reduction in spinal cord GAG (vs. 32% with weekly IT administration; FIG. 10B), and a 57% reduction in meningeal GAG (vs. 57% with weekly IT administration; FIG. 10C) compared with 4 untreated MPS I dogs. There was no significant difference in iduronidase or GAG levels with monthly vs. weekly IT rhIDU. As such, monthly intrathecal administration may be used.

Animals were tested for inflammatory response and for induction of tolerance. One dog developed a lymphoplasmacytic infiltrate in the meninges and a mild antibody response in blood and CSF. One dog had neurologic signs (see table below) at the start of treatment but these signs improved after 4 doses of monthly IT rhIDU with concurrent weekly IV rhIDU.

| BEFORE | AFTER |
|---|---|
| Lethargic | Alert |
| Ataxic gait | No ataxia |
| Gag reflex absent | Gag reflex present |
| Head tilt | No head tilt |

Figure 11A:
FIGS. 11A and 11B show comparison of GAG between untreated and intrathecally treated dogs. GAG storage is visibly reduced in perivascular cells, glia, and neocortical leptomeninges in treated dogs. The untreated samples (FIG. 11A) show foamy, swollen, GAG laden cells as contrasted with the treated samples shown in FIG. 11B which are thin cells with markedly less storage.
Figure 11B:
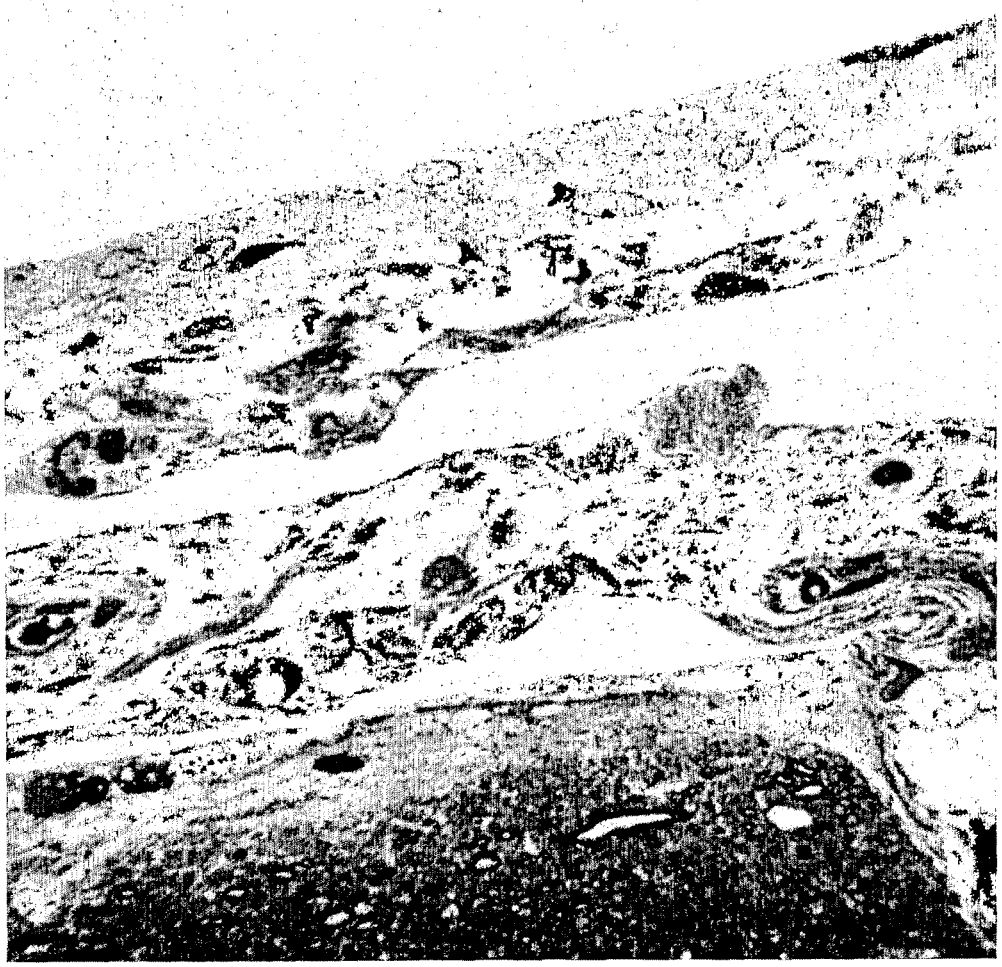
Figures 12A, 12B, 12C, 12D:
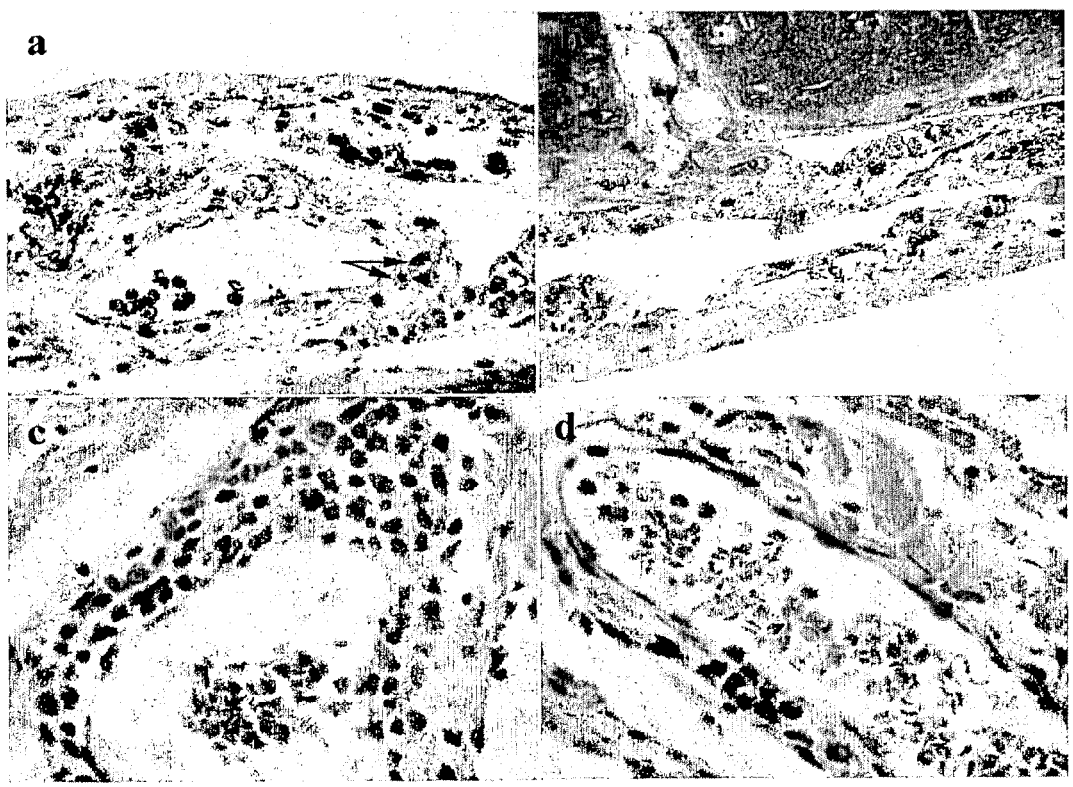
FIG. 12A through 12D shows that immune tolerance reduces the inflammatory response to intrathecally administered rhIDU. A lymphocytic and plasmocytic infiltrate develops in treated dogs (FIGS. 12A and 12C). Pre-conditioning with a regimen to induce immune tolerance greatly reduces this response (FIGS. 12B and 12D).

The second dog had been made tolerant to rhIDU using a novel method (described in e.g., co-owned U.S. application Ser. Nos. 10/141,668 filed May 6, 2002 and 10/429,314 filed May 5, 2003, (published as U.S. Patent Publication No. 20030211113 and U.S. Patent Publication No. 20040009906, respectively, each incorporated herein by reference in its entirety) and had little or no detectable immune response in blood and CSF and a very mild meningitis. Treated dogs had diminished leptomeningeal and perivascular GAG storage histologically. The fact that GAG storage is visibly reduced in perivascular cells, glia, and neocortical leptomeninges in IT treated dogs is depicted in FIG. 11A (untreated showing swollen, foamy, GAG-laden cells) and 11B (treated; thin cells with markedly less GAG storage). With respect to induction of tolerance, the data depicted in FIGS. 12A-12D shows that an animal that has been preconditioned with an immunosuppressive regimen and became tolerant to rhIDU exhibits a much milder immune response to the rhIDU therapy. FIGS. 12A and 12C show that in animals treated with rhIDU alone, a lymphocytic and plasmocytic infiltrate develops (FIGS. 12A and 12C). Pre-conditioning with a regimen to induce immune tolerance, on the other hand, greatly reduces this response (FIG. 12B and FIG. 12D).

These studies demonstrate that monthly IT rhIDU may be as effective as weekly IT rhIDU in correcting the lysosomal storage in brain and meninges of canine MPS.

The foregoing describes and exemplifies the invention but is not intended to limit the invention defined by the claims which follow.

I claim:

1. A method for treating Sanfilippo syndrome type B (Mucopolysaccharidosis type IIIB or MPS IIIB) comprising the step of administering intrathecally to a human subject in need of treatment a pharmaceutical composition comprising a fusion protein comprising recombinant human α-N-acetyl-glucosaminidase and a moiety that facilitates high uptake of a lysosomal enzyme, wherein the moiety is an IGF-II polypeptide that allows the lysosomal enzyme to bind to the mannose-6-phosphate receptor, and wherein the fusion protein is administered in an amount effective to ameliorate one or more central nervous system (CNS) symptoms of Sanfilippo syndrome type B.

2. The method of claim 1, wherein the intrathecal administration results in delivery of the fusion protein to one or more target brain tissues.

3. The method of claim 2, wherein the fusion protein is delivered to neurons, glial cells, perivascular cells and/or meningeal cells.

4. The method of claim 1, wherein the intrathecal administration results in reduction of lysosomal storage in brain target tissues.

5. The method of claim 1, wherein the intrathecal administration results in increased the fusion protein enzymatic activity in brain target tissues.

6. The method of claim 1, wherein the intrathecal administration results in reduced intensity, severity or frequency, or delayed onset, of at least one symptom or feature of MPS IIIB.

7. The method of claim 6, wherein the at least one symptom or feature of MPS IIIB is hearing loss, delayed speech development, deficits in motor skills, and/or mental retardation.

8. The method of claim 1, wherein the intrathecal administration takes place at an interval selected from once every week, once every month, and once every two months.

9. The method of claim 1, wherein the intrathecal administration is used in conjunction with intravenous administration.

10. The method of claim 1, wherein the intrathecal administration is not used in conjunction with intravenous administration.

11. The method of claim 1, wherein the intrathecal administration is used with immunosuppressive therapy.

12. The method of claim 1, wherein the intrathecal administration is used in absence of concurrent immunosuppressive therapy.

* * * * *